US009406130B2

(12) United States Patent
Vilsmeier

(10) Patent No.: US 9,406,130 B2
(45) Date of Patent: *Aug. 2, 2016

(54) DETERMINING AN ANATOMICAL ATLAS

(71) Applicant: Brainlab AG, Feidkirchen (DE)

(72) Inventor: Stefan Vilsmeier, Munich (DE)

(73) Assignee: Brainlab AG, Feldkirchen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/438,519

(22) PCT Filed: Oct. 26, 2012

(86) PCT No.: PCT/EP2012/071239
§ 371 (c)(1),
(2) Date: Apr. 24, 2015

(87) PCT Pub. No.: WO2014/063745
PCT Pub. Date: May 1, 2014

(65) Prior Publication Data
US 2015/0287198 A1    Oct. 8, 2015

(51) Int. Cl.
G06K 9/00    (2006.01)
G06T 7/00    (2006.01)

(52) U.S. Cl.
CPC ............ *G06T 7/0014* (2013.01); *G06T 7/0024* (2013.01); *G06T 2207/30004* (2013.01)

(58) Field of Classification Search
CPC .......... G06T 2207/30004; G06T 2207/30016; G06T 2207/30096; G06T 7/0024–7/0038; G06T 7/0014; G06K 9/6202–9/6215
See application file for complete search history.

(56) References Cited

U.S. PATENT DOCUMENTS

2010/0002921 A1* 1/2010 Fenchel ................. A61B 5/055
382/128

OTHER PUBLICATIONS

International Search Report and Written Opinion for International Application No. PCT/EP2012/071239 dated Feb. 28, 2013 (3 pages).
Christensen et al., "Synthesizing Average 3D Anatomical Shapes", Neuroimage, Academic Press, vol. 32, No. 1, Aug. 2006, pp. 146-158.
Ioannis et al., "Automatic Segmentation of Pediatric Brain MRIs Using a Maximum Probability Pediatric Atlas", Imaging Systems and Techniques, 2012 IEEE International Conference, Jul. 2012, pp. 95-100.
Ehrhardt et al., "Statistical Modeling of 4D Respiratory Lung Motion Using Diffeomorphic Image Registration", IEEE Transactions on Medical Imaging, vol. 30, No. 2, Feb. 2011, pp. 251-265.
Guimond et al., "Average Brain Models: A Convergence Study", Computer Vision and Image Understanding, Academic Press, vol. 77, No. 2, Feb. 2000, pp. 192-210.

* cited by examiner

*Primary Examiner* — Stephen R Koziol
*Assistant Examiner* — Timothy Choi
(74) *Attorney, Agent, or Firm* — Tucker Ellis LLP

(57) ABSTRACT

A data processing method for determining atlas data and comprises information on a description of an atlas image of a general anatomical structure. The method performed by a computer comprises: acquiring patient data which comprise a description of a set of images of an anatomical structure of a set of patient images and each patient image is associated with image representation parameters; acquiring model data which comprise information on a description of a model image of a model of an anatomical structure of a patient; determining matching transformations which are constituted to respectively match the set of patient images of the set of patients to the model image by matching images associated with the same parameter set; determining an inverse average transformation by applying an inverting and averaging operation to the determined matching transformations; and determining the atlas data.

18 Claims, 9 Drawing Sheets

MRDSα4 to MRDSα7

$$PMAVG^{-1} = w_1 \cdot [AVG\langle PM1, PM2, PM3\rangle]^{-1} +$$
$$w_2 \cdot AVG\langle PM1^{-1}, PM2^{-1}, PM3^{-1}\rangle$$
$$w_1 + w_2 = 1$$

Table 1

| atlas element | representation class |
|---|---|
| 1 | A |
| 2 | B |
| 3 | A |
| 4 | C |
| 5 | D |
| 6 | A |
| 7 | B |

Table 2

| representation class \ parameter set | α | β | γ |
|---|---|---|---|
| A | a | d | a |
| B | b | e | g |
| C | c | f | h |
| D | c | d | i |

S123 acquiring a description of representation data sets

Table 3

| representation data set | representation information (visual appearance) |
|---|---|
| a | ▨ |
| b | ∣∣∣∣ |
| c | ≡ |
| ⋮ | |
| g | ╲╲╲ |
| h | ╱╱╱ |
| i | ▦ |

S124 acquiring the determination rule by performing the steps of:

- selecting a representation class on the basis of an atlas element identifier, using Table 1;

- determining a representation data set on the basis of the selected representation class and the parameter set associated with the patient image, using Table 2;

- determining the representation of the atlas element on the basis of the determined representation data set, using Table 3.

Figure 3B

DETERMINING AN ANATOMICAL ATLAS

RELATED APPLICATION DATA

This application is a national phase application of International Application No. PCT/EP2012/071239 filed Oct. 26, 2012 and published in the English language.

The present invention is directed to determining data which are referred to as atlas data. Atlas data comprise information on a description of an image of a general anatomical structure. This image is referred to as the atlas image. The atlas data describe an anatomical atlas which in turn describes the general anatomical structure.

The present application is related to the parallel filed application entitled "Matching Patient Images and Images of an Anatomical Atlas". The content of this parallel application is correspondingly included in the description of the present application in a section headed "Matching Patient Images and Images of an Anatomical Atlas". This section of the description is referred to in the following as the "matching section". The present application as a whole uses the same definitions of terms used in the matching section. The portion of the present description preceding the matching section is referred to as the "improvement section". The method described in the matching section is also referred to in the following as the "matching method".

The object of the present invention is to determine the aforementioned atlas data. This object is achieved by the subject matter of the independent claims. The dependent claims are directed to advantageous embodiments. Advantages, advantageous features, advantageous embodiments and advantageous aspects of the present invention are disclosed in the following. Different advantageous features can be combined in accordance with the invention wherever technically sensible and feasible. A feature of one embodiment which is functionally identical or similar to a feature of another embodiment can in particular replace said latter feature. A feature of one embodiment which supplements a function of another embodiment can in particular be added to said other embodiment.

The atlas data are determined on the basis of model data which can for example be understood to be data which represent a starting point for determining the atlas data and/or understood to be atlas data which can be the subject of improvement. The section of the present description which relates to determining the atlas data is correspondingly referred to as the "improvement section".

The atlas data describe information on a general anatomical structure (see also the matching section in this respect). This information on a description of an image of a general anatomical structure can be the atlas image or information contained in the atlas image, i.e. the spatial information (position and/or geometry) of the general anatomical structure, in particular spatial information on the anatomical elements of the general anatomical structure (for a more detailed definition of "spatial information", see the matching section below). The information on a description of the image of the general anatomical structure can also be information on the representation of anatomical elements which are represented in the atlas image, i.e. the information on a description of the image of the general anatomical structure can in particular be the information referred to in the matching section as "element representation information". In the present improvement section, this information is referred to as "atlas element representation information" in order to differentiate the "atlas element representation information" discussed here from the "model element representation information" mentioned further below in the matching section. More specifically, the atlas element representation information is in particular the information referred to in the matching section as "representation data sets" and in the present improvement section as "atlas representation data sets".

The present method is in particular a data processing method as described in the matching section. The term "acquiring" is also understood in the present improvement section within the meaning described in the matching section below, as are other terms such as "computer".

The method advantageously comprises a step of acquiring patient data. The patient data are defined as comprising a description of a set of images of an anatomical structure of a set of patients. The images are referred to as patient images (see also the matching section in this respect). In particular within the context of the present improvement section, the patients can differ from each other, i.e. a plurality of patient images can be from a plurality of different patients. The purpose of this is to ultimately arrive at atlas data which represent the anatomical structure of an average patient, i.e. the "general anatomical structure" can be understood as representing the anatomical structure of an average patient. As described in the matching section further below, each patient image is associated with a parameter set. The parameter sets are defined in more detail in the matching section. The method described in the present improvement section is also referred to as the "improvement method", since the aim of the method is to determine atlas data which represent an improvement on the model data in terms of the information they describe.

The improvement method preferably comprises a step of acquiring model data. The model data can be identical to the atlas data described in the matching section if the "matching method" is used to match patient images to model images in order to improve the atlas data, i.e. the PM transformation described immediately below corresponds to the PA transformation described in the matching section. To this end, it is merely necessary to replace the term "atlas" in the matching section with "model" in order to "transform" the description determining the PA transformation into a description of determining the PM transformation. The model data comprise information on a description of the image of a model of an anatomical structure of a patient. This information can be the model image or information represented by the model image, i.e. the information on the description of the image of the model can be (in particular only) spatial information on the structure of the model (also referred to as the "model structure"). The model structure is the anatomical structure represented in the model image. The information on a description of the image of the model can also be information on the representation of the model structure. The information on a description of the image of the model can in particular be the above-mentioned element representation information on a description of the representation of elements of the model structure referred to as "model elements". This information is therefore also referred to as "model element representation information". The model element representation information has the same properties as those described in the matching section with respect to the element representation information. The model data can in particular describe an anatomical atlas which is to be improved, and the model structure can describe a general anatomical structure which is to be improved by the improvement method.

The model image can be a patient image of a patient who preferably exhibits an average anatomical structure. The model image can be the result of an averaging process in which patient images are averaged. The averaging process can in particular be the process described in this section by the "improvement method" and can in particular comprise an averaging and inverting operation. The model image and in particular the model structure can be based on a generic model of an anatomical body structure. A user can for example generate structures for different anatomical elements by referring to known atlases which respectively describe the different anatomical elements. The representation of the anatomical elements can also be generated by a user, in particular for different parameter sets, by referring to patient images and/or atlases which represent the model element in different patient images or atlases associated with different parameter sets.

The improvement method preferably also comprises a step of determining matching transformations (see also the matching section in this respect). These transformations are referred to as PM transformations, since they perform a transformation from the patient images to the model images, in particular using image fusion (see also the matching section in this respect). This PM transformation corresponds to the PA transformation described in the matching section as a transformation from the patient image to the atlas image. The PM transformations respectively match the patient images of the set of patients, in particular the plurality of patient images of the plurality of patients, to a set of model images by matching images associated with the same parameter set. Matching is preferably performed by a plurality of PM transformations. The set of patient images preferably comprises a plurality of patient images. The plurality of patient images can in particular be patient images of a plurality of different patients, i.e. the set of patients comprises a plurality of patients. Alternatively or additionally, the set of patient images comprises a plurality of patient images which represent the same patient, and the plurality of patient images are associated with different parameter sets. The patient images can in particular be images of a plurality of different patients and comprise more than one patient image from one or more of the different patients. If there are multiple patient images, then these patient images can be associated with the same parameter set or with different parameter sets. There is preferably more than one image to be matched, which implies that more than one PM transformation is determined. This allows an averaging operation to be applied in the next step of the improvement method, in which the averaging operation averages different image information from the same patient in order to amend the atlas data and/or averages image information from different patients which can all be associated with the same parameter set or with different parameter sets. Preferably, each PM transformation matches images associated with the same parameter set, i.e. the model image and the patient image to be matched by the PM transformation are both associated with the same parameter set.

The improvement method preferably comprises a step of determining an inverse average transformation using the PM transformations mentioned above. The inverse average transformation is preferably determined by applying an inverting and averaging operation to the determined PM transformations. The way in which the inverting and averaging operation can be applied is described in more detail below.

In another step (referred to as "atlas determination step") of the improvement method, the inverse average transformation is used to determine the atlas data. To this end, the determined inverse average transformation is applied to the model data, in particular to at least one of the model image, the spatial information on the model data and the model element representation information.

In accordance with the above-described atlas determination step, the representation information included in the atlas is preferably determined on the basis of the model element representation information. In accordance with an alternative version of the atlas determination step, the determined PM transformations are applied to the patient images in order to determine matched patient images. Due to matching, the matched patient images preferably all have the same geometry. In the next step, the matched patient images are averaged. This means in particular that the representation information described by the matched patient images is averaged (since their geometry is preferably identical, due to matching). To this end, average (for example, mean or mode) values of grey values are determined for a plurality of positions (sub-regions) within the anatomical elements represented by the matched patient images. The averaging step thus results in an average matched patient image. In another step, the atlas data are then determined by applying the determined inverse average transformation to the average matched patient image. The average matched patient image thus represents an average of the patient images. This average is achieved by performing the above-described steps and in particular by using the inverse average transformation. The average matched patient image in particular reflects an average of the representation information of the patient images.

The above-mentioned inverse average transformation can be determined by applying an inverting and averaging operation. The sequence in which the inverting and averaging operation is applied can vary. In accordance with one embodiment, inverting operations are applied to the determined PM transformation in order to determine inverse PM transformations, in particular a plurality of inverse PM transformations. The determined inverse PM transformations are then averaged by applying an averaging operation. The result of the averaging operation is then the inverse average transformation, i.e. the inverse average transformation represents an average of the inverse PM transformations.

In accordance with another embodiment, an averaging operation is first applied to the PM transformations (in particular a plurality of PM transformations). This results in an average PM transformation. An inverting operation is then applied to the average PM transformation in order to invert the average PM transformation. The resultant transformation is the inverse average transformation. These two methods for determining the inverse average transformation can be combined (see the detailed description).

As mentioned above, the patient data can comprise a plurality of patient images associated with the same parameter set. For explanatory purposes, this parameter set is referred to here as the common parameter set. In accordance with this embodiment, the model data comprise a model image which is associated with the aforementioned common parameter set, or such a model image is determined on the basis of the model data, for instance in the same way as an atlas image is determined (as described in the matching section). Matching can thus, as is preferred, match images associated with the same parameter set. In particular, the patient images associated with the common parameter set are respectively matched by a PM transformation to the model image associated with the (same) parameter set. In this embodiment, the atlas data are determined by determining the inverse average transformation, by applying the inverting and averaging operation to the determined PM transformations. The atlas data are then determined by applying the determined inverse average transformation to the model image associated with the common parameter set, in order to determine the atlas image associated with the common parameter set. The atlas image includes additional information from the patient images, in addition to the information represented by the model image.

As mentioned above, the model data preferably comprise the model element representation information. In accordance with one embodiment, the model element representation information also describes a determination rule. This is analogous to the element representation information described in the matching section. Preferably, the determination rule described by the model element representation information is in particular the same as the determination rule described in the matching section (in connection with the atlas element representation information). Further details regarding the determination rule are given in the matching section. The determination rule is used to determine the model representation data sets. The model representation data sets correspond to the representation data sets described in the matching section. As described by the determination rule, the model representation data sets are assigned to model elements in accordance with the parameter set with which the model image is to be associated. Preferably, the model image is associated with the same parameter set as the patient images which are to be subjected to the PM transformations in order to match them to the model image. The model data preferably allow different model images associated with different parameter sets to be determined using the model element representation information (in particular, the determination rule) and the model spatial information which in particular describes (and in particular only describes) the positions and/or geometries of the model elements. This is analogous to determining atlas images, as described in the matching section. Determining the atlas image on the basis of the atlas data and the patient data, as described in the matching section, in particular corresponds completely to determining the model image on the basis of the model data and the patient data. The model image is thus preferably determined on the basis of corresponding model elements. The corresponding model elements in particular do not represent the complete model structure but only a part of it. This allows parts of the atlas data to be improved which relate to a part of the general anatomical structure only, in particular the atlas spatial information relating to atlas elements which correspond to the model elements. The term "corresponding" as used here is defined in the matching section and refers to an anatomical correspondence, as described in said section. The same applies to the correspondence between the model elements and the patient elements. By matching the corresponding elements, the anatomical atlas described by the atlas data can be improved, part by part, by improving the atlas spatial information on some of the atlas elements and/or by improving the atlas element representation information, in particular the atlas representation data sets, for at least said corresponding atlas elements. The model elements are preferably classified in the same way as the atlas elements are classified into representation classes (see also the matching section in this respect). This means that an improvement in a representation data set for an atlas element which belongs to a particular representation class results in an improvement in the representation data set of all the other elements belonging to the same representation class, since the representation data set in question is the same. With respect to the concept of representation classes in general, reference is made to the matching section. The representation classes are preferably also used in the improvement method. In particular, the determination rule described by the model element representation information uses the representation classes in the same way as is described in the matching section.

As mentioned above, the atlas data can in particular be determined by determining the atlas spatial information and/or the atlas element representation information. Both the atlas spatial information and the atlas element representation information can be used to determine atlas images for different parts of the body which are in particular associated with different parameter sets, as described in the matching section. The representation classes are preferably used for this purpose, as described in the matching section.

As mentioned above, the PM transformations and/or the inverse average transformation can be restricted to a part of the model structure, in particular to the corresponding model elements, i.e. applying the inverse average transformation to the corresponding model elements allows corresponding atlas elements to be determined, which in particular improves the corresponding atlas elements, wherein "improved" as used here means in particular that the spatial information is refined and/or that the representation data sets involved are improved.

If different parameter sets are associated with different patient images, then different inverse average transformations can preferably be determined, wherein each of the different inverse average transformations is associated with one of the different parameter sets. This is preferably performed for the purpose of determining the atlas representation data sets, since the model element representation data sets vary in accordance with the parameter sets and since the atlas element representation data sets are a result of applying the inverse average transformation to the model element representation data sets. In other words, different inverse average transformations are determined in order to be respectively applied to different model element representation information in order to respectively determine different atlas element representation information, i.e. the determined atlas element representation information is respectively assigned to a respective parameter set.

In order to determine the different inverse average transformations, the averaging operation is preferably applied to the PM transformations or the inverse PM transformations separately for the different parameter sets, i.e. the PM transformations which are associated with the same parameter set are averaged or the inverse PM transformations which are associated with the same parameter set are averaged.

Alternatively or additionally, the part of the PM transformations which relates to transforming the spatial information is averaged, even if the PM transformations relate to different parameter sets, i.e. the PM transformations are averaged or the inverse PM transformations are averaged. The background to this is that transforming the spatial information is not generally influenced by the parameter set (see also the matching section in this respect, in particular with regard to distortions caused by analytical devices). The spatial information included in the patient images can vary with respect to particular patient elements in accordance with the parameter set. The averaging operation applied to the PM transformations or inverse PM transformations is therefore preferably weighted in accordance with the amount of image information included in the patient images. The weighting is in particular dependent on the position and in particular dependent on the patient element. In other words, the local amount of underlying image information is preferably used to determine the weighting for the spatial information included in patient images associated with different parameter sets. The weighting can in particular depend on the type of patient element in combination with the parameter set. The image information of a particular patient element is for example given a different weighting depending on the parameter set associated with the patient image in which the patient element is present. A patient element representing a bone structure is for example assigned a higher level of image information if the parameter set refers to an x-ray image (such as a CT image) than if the parameter set refers to a magnetic resonance image (MRI). As mentioned above, representation classes are preferably used to classify the model elements to which the patient elements are to be matched. The local weighting for the averaging operation can be determined in accordance with the representation class of the model segments to which the patient element is to be matched, in combination with the parameter set. The term "local weighting" refers to the part of the averaging operation which relates to the model segment. As an alternative to weighting or in addition to weighting, PM transformations relating to the same patient elements of the same patients but to different parameter sets can be modified by coupling the determinations described by these PM transformations, in the way described in the matching section, before the averaging and inverting operation is applied.

As described in detail in the matching section, a deformation described by matching sub-transformations (the matching section discusses AP sub-transformations as an example of matching sub-transformations) can be coupled. As mentioned above, this coupling can also be used in the improvement method. Coupled PM transformations which match different patient images of the same patient to one or more model images which exhibit identical spatial information are preferably determined by taking into account the coupled deformation, as described in the matching section for AP sub-transformations, i.e. by taking into account the fact that the spatial information described in these same model images is identical and by also taking into account information on the spatial correlation between the spatial information described in the different patient images of the same patient (but associated with different parameter sets). Thus, coupled PM transformations are preferably considered to be matching sub-transformations and are determined by taking into account the fact that the deformations described by the coupled PM transformation are coupled in the way described in the matching section. The coupled PM transformation is also determined in accordance with the procedure described in the matching section, the difference with respect to APT1 and APT2 being that the direction of matching is not from the atlas image to the patient image but rather from the patient image to the model image (for the PM transformations).

In accordance with another embodiment, the model data comprise spatial flexibility information which is the same as the spatial flexibility information described in the matching section with respect to the atlas data, i.e. the spatial flexibility information describes a flexibility of the position of model elements within the model structure. The PM transformations are also determined on the basis of the spatial flexibility information. Anatomical variability can also be taken into account, in that the model data describe a number (in particular a plurality) of different model structures for different anatomical states (such as for example male, female, position of extremities and/or organs, etc.). The model data can in particular describe a plurality of states of the same anatomical structure, i.e. they can in particular be time-dependent, as described in the matching section with respect to the atlas data.

Advantageously, data are acquired which describe the corresponding model elements. These data are referred to as model correspondence part data. The model correspondence part data describe the corresponding model elements. The model correspondence part data correspond to the "correspondence part data" described in the matching section.

The model correspondence part data can be determined in the same way as is described in the matching section for the correspondence part data, i.e. the atlas elements correspond to the model elements and the general anatomical structure corresponds to the model structure. The model correspondence part data in particular allow the model elements to be selected which are subjected to the PM transformations. Coarse spatial information referred to as "coarse model spatial information" is preferably acquired for this purpose. The coarse model spatial information corresponds to the "coarse atlas spatial information" mentioned in the matching section. The coarse model spatial information describes the spatial information on the model structure in less detail than the model spatial information used for determining the model image set. Using the coarse model spatial information reduces the data processing load, as described in the matching section with respect to the coarse atlas spatial information. Rigid matching transformations can in particular be applied in order to perform rigid matching between a part of the model structure—which is described by the coarse model spatial information and which in particular coarsely describes the model elements—and the patient images. The model correspondence part data in particular allow a part of the atlas data to be improved which relates to the corresponding model elements described by the model correspondence part data.

The present invention is also directed to a program which is in particular run on a computer or loaded onto a computer and which performs the steps of the improvement method described here. The present invention is also directed to a program storage medium which stores the program and to a computer on which the program is run or into the memory of which the program is loaded. The present invention is also directed to a signal wave which carries information representing the program.

The present invention is also directed to a medical image processing system which comprises the aforementioned computer and an analytical device for generating patient images of patients. The computer is used to determine the atlas data on the basis of the generated patient images (example see FIG. 5).

Patient data can describe two-dimensional or three-dimensional images. The two-dimensional or three-dimensional images can also be time-dependent and/or can describe different states of the same body, as described in the matching section with respect to time-dependent two-dimensional or three-dimensional atlases.

The patient data and the atlas data can describe an anatomical structure of an average healthy patient. However, the patient data and the atlas data can also describe an anatomical structure which exhibits pathological changes vis-à-vis the healthy anatomical structure. The following section "Pathological Changes" refers to this aspect and also describes an embodiment of the "improvement method".

Pathological Changes

The patient data can describe images of patients which exhibit pathological changes to the anatomical structure, for instance patients with one or more tumours. The method described here is preferably used to establish a statistical spatial distribution of pathological changes, in particular for example of tumours within parts of the body in accordance with the type of tumour, i.e. for example, a plurality of patients with a particular type of breast cancer (in accordance with a particular tumour classification) or a particular type of prostate cancer (in accordance with a particular tumour classification) are analysed in order to generate patient images.

The type of cancer and the class of tumour represent examples of meta data referred to as patient patho meta data. The patient patho meta data specify and in particular classify the pathological changes to the general anatomic structure using parameters referred to as "patho parameters", in particular in accordance with established classifications such as the TNM Classification of Malignant Tumours. The model data described here can be model data which describe an average patient exhibiting the same type of pathological changes (for example, cancer) or can be model data which describe a healthy patient. The PM transformations from the patient images to the model image are then performed as described in this document. The inverse average transformation is then determined, after which the atlas data are determined. These atlas data then describe a statistical distribution of the pathological changes (for example, tumours) within a patient's body which is based on the original model data and the patient data. If the original model data describe a healthy patient, the statistical distribution of the pathological changes is based on the spatial distribution of the pathological changes in the plurality of patient images which are matched to the model image. If the model data already describe a pathological anatomical structure of the corresponding type of tumour, then they are adapted on the basis of the plurality of patient images. In this way, atlas data can be determined which describe a statistical distribution of pathological changes, in particular tumours. In accordance with one embodiment, the representation information included in the plurality of patient images is also subjected to the inverse average transformation. In accordance with another embodiment, the pathological changes (for example, tumours) are identified in the patient information as separate structures and in particular segmented, and only the structures which represent pathological changes are subjected to the PM transformations. If one or more pathological changes (for example, tumours) are distributed over a plurality of anatomical elements, the PM transformation is preferably applied to the plurality of anatomical elements (patient elements) in order to obtain a statistical distribution of pathological changes (for example, tumours) over the plurality of model elements and, ultimately, atlas elements. The example given above referring to tumours also applies to any other kind of pathological changes in a patient's body. Thus, the atlas data described here can describe not only a healthy patient but also any particular type of patient, where the particular type of patient is in particular characterised by a pathological change in the anatomical structure of the patient. Thus, the atlas data preferably describe a plurality of different general anatomical structures, each in accordance with different patho parameters.

In accordance with one embodiment, all the patient images subjected to the averaging process (which uses the inverse average transformation) are associated with the same patho parameter described by the patient patho meta data. The model data can be model data which describe spatial information only and do not include representation information or only include representation information which does not reflect pathological changes. The representation information for an anatomical element is then for example homogeneous all the entire anatomical element, without reflecting any pathological changes within the anatomical element such as tumours. Model data of this type are referred to here as "neutral model data", since they do not reflect pathological changes. The patient images can be subjected to the method described here using neutral model data in order to determine atlas data which reflect pathological changes in accordance with a patho parameter. This procedure is preferably repeated for a plurality of different patho parameters, i.e. a plurality of sets of patient images (each set of images being assigned to a particular patho parameter) is subjected to the improvement method in order to determine atlas data which describe a plurality of different pathological general anatomical structures, wherein each pathological structure is assigned to a particular patho parameter.

In accordance with another embodiment, the model data comprise information on a description of a plurality of images of a plurality of models of a plurality of anatomical structures which are respectively assigned to a particular patho parameter, i.e. the model data comprise a plurality of patho model data, each describing an image of a model of an anatomical structure which has undergone a pathological change in accordance with a particular patho parameter. The corresponding model image is thus associated with the particular patho parameter. The patho model data which are associated with the same patho parameter are preferably selected from said plurality of patho model data on the basis of the patient patho meta data (assigned to the plurality of patient images). The atlas data which are ultimately determined on the basis of the patho meta data associated with a particular patho parameter are atlas data which improve the patho model data associated with the particular patho parameter. Atlas data of this type are referred to as patho atlas data. The atlas data in particular comprise a plurality of patho atlas data, each of which is respectively assigned to a patho parameter and describes the pathological changes in a general anatomical structure in accordance with the patho parameter. Since the patho atlas data are determined on the basis of the improvement method in accordance with the invention (which uses an averaging process), the patho atlas data in particular describe a statistical (spatial) distribution of pathological changes within the general anatomical structure. This is in particular the case if the parameter set describes an imaging method which allows tumours to embedded detected, such as for instance PET. The atlas data can be used to generate a PET image of a general anatomical structure which is associated with the particular patho parameter. The patho atlas data can thus be used as a basis for planning for instance radiotherapy.

Additional features are disclosed in the following description of embodiments. Different features of different embodiments can be combined.

FIGS. 1A, B show an embodiment of the method according to the present invention.

FIG. 1C shows an optional additional step in the method according to the present invention.

In accordance with one embodiment, the method comprises an initial step S210 in which patient data are acquired. The corresponding example given to the right of S210 shows a patient image of a patient x associated with the parameter set α, which is correspondingly referred to as PIxα, a patient image of a patient y associated with the same parameter set α, which is correspondingly referred to as PIyα, and a patient image of a patient z associated with the same parameter set α, which is correspondingly referred to as PIzα.

In the method according to the invention, model correspondence part data are also acquired (S220) which describe the model elements corresponding to the patient elements shown in the patient images PIxα, PIyα and PIzα. In the example given, the model correspondence part data indicate the model elements 4 to 7 for the patient image PIxα, the model elements 3 to 7 for the patient image PIyα, and the model elements 4 to 8 for the patient image PIzα. The method preferably determines model elements which are represented in all of the patient images. In the example given, the model elements 4 to 7 are corresponding model elements for all of the patient images. The method preferably comprises a step in which the corresponding model elements are selected which are common to all the patient images and which are then referred to as the common corresponding elements and are to be used in determining the atlas data (i.e. used in the subsequent steps).

In another step S230, the model data are acquired. Preferably, spatial information with respect to the common corresponding model elements is acquired. In the example given, the spatial information on the model elements 4 to 7 is in particular acquired by referring to the model correspondence part data and performing the above-mentioned selecting step (see Sub-step S231 in FIG. 1A). An example of the acquired (in particular, determined) spatial information is given to the right of Sub-step S231. The spatial information describes the geometries of the model elements 4 to 7 and their relative positions.

The model representation data sets (MRDS) are preferably determined for the common corresponding model elements in another sub-step S232. The model representation data sets are dependent on the parameter set and the corresponding model element. The model representation data sets are preferably determined in accordance with the determination rule. In the example given, the model representation data set for the model element 4 and the parameter set α is denoted as MRDSα4, the model representation set for the model element 5 and the parameter set α is denoted as MRDSα5, the model representation data set for the model element 6 and the parameter set α is denoted as MRDSα6, and the model representation data set for the model element 7 and the parameter set α is denoted as MRDSα7.

In Sub-step S233, the model image is determined on the basis of the spatial information on the common corresponding model elements and the model representation data sets. An example is given to the right of S233 in FIG. 1A. The model image shown is denoted as MIα(4-7). Hatched lines indicate the different grey values described by the model representation data sets MRDSα4 to MRDSα7.

Step S240 relates to determining the matching transformations. Examples of matching transformations, namely PM1, PM2 and PM3, are given to the right of S240. The matching transformation PM1 matches the patient image PIxα to the model image MIα(4-7), the matching transformation PM2 matches the patient image PIyα to the model image MIα(4-7), and the matching transformation PM3 matches the patient image PIzα to the model image MIα(4-7). Thus, patient images from different patients associated with the same parameter set are matched to the same model image by using the different matching transformations PM1, PM2 and PM3. In Step S250, the inverse average transformation (PMAVG$^{-1}$) is determined. As described above, the inverse average transformation can be determined by applying first an averaging operation and then an inverting operation. An example of this is given in the first line of the equation shown to the right of S250. The result of these operations can then be multiplied by a weighting factor $w_1$. Alternatively, the inverse average transformation is determined by first applying the inverting operation to PM1, PM2 and PM3 and then averaging the determined inverse transformations PM1$^{-1}$, PM2$^{-1}$ and PM3$^{-1}$. The sum of these is shown in the second line of the equation to the right of S250 and is multiplied by the weighting factor $w_2$. The third line of the equation shows the condition that the sum of the weighting factors should be 1.

Step S260 relates to determining the atlas data. The atlas data can be represented by an atlas image, as for example in Sub-step S261 in FIG. 113. The atlas image is determined by applying the inverse average transformation PMAVG$^{-1}$ to the model image MIα(4-7). This results in the atlas image AIα (4-7). To the right of this, an alternative example is given in which an atlas image is to be determined which is larger than AIα(4-7), in which case the transformation PMAVG$^{-1}$ is applied to a correspondingly larger model image MIα($n_1$-$n_2$), where $n_1$<4 and $n_2$>7, i.e. a larger number of model elements is represented than in AIα(4-7).

The inverse average transformation PMAVG$^{-1}$ is applied to the spatial information and the representation of the model elements 4 to 7. The inverse average transformation PMAVG$^{-1}$ is not necessarily applied to the representation of model elements outside the model elements 4 to 7, but can be applied to these. At the boundary between a complex of model elements 4 to 7 and model elements outside the complex, the inverse average transformation PMAVG$^{-1}$ can in particular result in a shift in said boundary. The inverse average transformation PMAVG$^{-1}$ can also be applied to the representation of other model elements which belong to the same representation class as the model elements 4 to 7 but differ from the model elements 4 to 7. If the geometry and position of the boundary of the complex of model elements 4 to 7 is not changed by applying PMAVG$^{-1}$, and if the concept of representation classes (or another similar concept) is not applied, then the spatial information and the representation of the atlas elements in AIα($n_1$-$n_2$) which are not the atlas elements 4 to 7 are preferably identical to the corresponding model elements and their representation.

Sub-step S262 relates to an embodiment in which determining the atlas data corresponds to determining atlas spatial information. In the examples given to the right of this step, the spatial information of the atlas elements 4 to 7 is determined by applying the inverse average transformation PMAVG$^{-1}$ to the model elements (the model elements can also be referred to as "white model elements", in a similar way to the white atlas elements described in the matching section). To the right of this example, another example is shown in which model elements $n_1$ to $n_2$ are subjected to the inverse average transformation PMAVG$^{-1}$. This results in atlas elements $n_1$ to $n_2$, but the inverse average transformation PMAVG$^{-1}$ has preferably only been applied to the model elements 4 to 7, i.e. the other elements are not altered, at least providing they are not at the boundary between the complex consisting of the model elements 4 to 7 (and/or other elements, as applicable).

Sub-step S263 relates to determining atlas representation data sets. In the example given to the right of S263, the model representation data sets MRDSα4 to MRDSα7 are transformed into the atlas representation data sets ARDSα4 to ARDSα7 by means of the inverse average transformation PMAVG$^{-1}$. FIG. 1C shows an optional addition to Sub-step S263 which is explained further below.

Step S270 relates to repeating the "improvement method". To this end, the atlas data determined in Step S260 are used as new model data when Step S230 is repeated. Moreover, when repeating the improvement method, new patient data—in particular, new patient images—are preferably used when Step S210 is repeated. Inputting new patient data then results in a step-by-step improvement of the atlas data.

FIG. 1C shows an optional addition to Sub-step S263 which is denoted as S263'. In this sub-step, representation classes are used. Firstly, the representation classes are identified, for example by using a table (such as Table 1 as described in the matching section). In the example given to the right of S263', the model element 4 belongs to the representation class A and the model element 7 belongs to the representation class B.

New representation data sets are then assigned to the combinations of representation classes and parameter sets, i.e. in the example given, the atlas representation data set ARDSα4 determined in Sub-step S263 is assigned to the combination of the representation class A and the parameter set α. The atlas representation data set ARDSα7 is assigned to the combination of the representation class B and the parameter set α as a new representation data set. The results of this is that the representation data set ARDSα4 will be used for the representation of not only the atlas element 4 but also any atlas element which belongs to the representation class A and is associated with the parameter set α. Correspondingly, the representation data set ARDSα7 will be used to determine the representation of not only the atlas element 7 but also any atlas element which belongs to the representation class B and is associated with the parameter set α.

FIG. 2 shows a PM transformation being applied in order to determine an average atlas element which represents an average of spatial distributions of pathological changes represented in patient images of different patients associated with the same patho parameter. Patient elements 50 and 52 are shown on the right in FIG. 5. The patient element 50 includes a sub-region 51 exhibiting a grey level 200 which deviates from the usual grey level 0 in the remaining area of the patient element 50. Similarly, the patient element 52 includes a sub-region 53 exhibiting a grey level 200 which deviates from the usual grey level 0 in the remainder of the patient element 52. The patient elements 50 and 52 are anatomically corresponding elements and are from patients associated with the same patho parameter. The patient elements 50 and 52 are thus included in patient images associated with the same patho parameter and preferably associated with the same parameter set. The PM transformation PM1 matches the patient element 50 to a model element (not shown). The PM transformation PM2 matches the patient element 52 to the same model element. The PM transformations are thus determined. The inverse average transformation is then determined and applied to the model element (not shown). The resulting atlas element 60 is shown on the left in FIG. 5. The atlas element 60 includes two areas 61 and 63 exhibiting a grey level 100 which deviates from the otherwise usual grey level 0 in the atlas element 60. The grey level 100 is half the magnitude of the grey level 200 in the sub-regions 51 and 53 of the patient elements 50 and 52 due to the averaging process and can be considered to represent a spatial statistical distribution of pathological changes in the areas 61 and 63. The interior of the atlas element 60 thus represents a spatial probability distribution of pathological changes, wherein the probability is dependent on the position within the atlas element 60.

Matching Patient Images and Images of an Anatomical Atlas

The invention also relates to determining a transformation (a matching transformation) which (in particular non-rigidly) matches a set of one or more images of an anatomical body structure of a human or animal patient and a set of one or more images of a general anatomical structure of a patient model as described by an anatomical atlas, by matching respective images of the sets to each other, in particular using image fusion, wherein the respective images are associated with the same parameter set (see below) and represent one or more anatomical elements which are matched to each other and correspond to each other.

The anatomical atlas (or "atlas" for short) describes the general anatomical structure of the complete body of a patient model or an object in the patient model or in particular a plurality of objects in the patient model which in particular have a defined positional relationship with respect to each other. An object can comprise one or more anatomical elements. The atlas can be a two-dimensional or three-dimensional (static) atlas or a time-dependent two-dimensional or three-dimensional atlas (a so-called 4D atlas).

A data processing method is advantageously provided for determining the matching transformation. The matching transformation matches a set of one or more images of an anatomical body structure of a patient and a set of one or more images of a general anatomical structure. The set of one or more images of the anatomical body structure of the patient is referred to as the patient image set. The anatomical body structure comprises anatomical elements as sub-structures. The set of one or more images of the general anatomical structure is referred to as the atlas image set. As described below, the atlas image set is determined (in particular generated) in accordance with patient data including one or more parameter sets and on the basis of atlas data. Determining the atlas image set is thus flexible and can be adapted to the particular situation presented by the patient data. The particular situation presented by the patient data is in particular defined by the anatomical elements represented in the patient images, which are referred to as the patient elements, and by at least one parameter set which is associated with the patient image set. A parameter set represents and in particular comprises parameters which have an influence on (generating) an image ("patient image") of an anatomical body structure (by means of an analytical device). In particular, the parameters have an influence on the representation, in particular the visual appearance, of the anatomical body structure (in particular the anatomical elements) in the (patient) image. The parameters are therefore also referred to as "representation parameters". The parameter set represents and in particular comprises parameters which describe the type of an analytical device and in particular measurement parameters of the analytical device. One example of a representation parameter is a particular image modality used for generating the patient image set. One particular example of a representation parameter is a DICOM (Digital Imaging and Communications in Medicine). The patient image set can of course also or instead comprise patient images associated with other representation parameters, in particular different image modalities such as computer tomography (CT) and magnetic resonance (MR). The image modalities are in particular further specified by means of measurement parameters used for adjusting the analytical device, such as the voltage or magnetic field strength. The measurement parameters are also an example of representation parameters. There may be many different parameters involved when generating an analytical image of an anatomical structure by means of an analytical device, all of which constitute examples of representation parameters. The representation of patient elements in patient images can for example depend on the magnetic field strengths used during MR, the repetition time, the echo time, the inversion time, the flip angle, etc.

In the field of medicine, imaging methods (imaging modalities) are used to generate image data (for example, two-dimensional or three-dimensional image data) of anatomical structures (such as soft tissues, bones, organs, etc.) of the human body. The term "medical imaging methods" is understood to refer to imaging methods, advantageously apparatus-based imaging methods (so-called medical imaging modalities, in particular radiological imaging methods), such as for instance computer tomography (CT) and cone beam computer tomography (CBCT; in particular, volumetric CBCT), x-ray tomography, magnetic resonance tomography (MRT or MRI=magnetic resonance imaging), in particular $T_1$-weighted MRI, $T_2$-weighted MRI, PET (with and without contrast agent), conventional x-ray, sonography and/or ultrasound examinations. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body.

In order to determine the geometry and/or position of an anatomical body structure, analytical devices such as x-ray devices, CT devices or MRT devices are used to generate analytical images (such as x-ray images or MRT images) of the anatomical body structure. Analytical devices in particular use imaging methods and are in particular devices for analysing a patient's body, for instance by using waves and/or radiation and/or energy beams, in particular electromagnetic waves and/or radiation, ultrasound waves and/or particle beams. Analytical devices are in particular devices which generate images (for example, two-dimensional or three-dimensional images) of the patient's body (in particular, the anatomical body structure of the patient's body) by analysing the body. Analytical devices are in particular used in medical diagnosis, in particular in radiology.

The above-mentioned parameter sets represent and in particular comprise one or in particular more (representation) parameters (such as the type of analytical device and magnetic field strength in MRT devices or the voltage in CT devices) which reflect (and in particular are) parameters which have an influence on the representation of the patient elements in the patient image, in particular when generating the patient image. Thus, each of the patient images is associated with a particular parameter set. Different patient images can be and in particular are associated with different parameter sets. The parameters which the parameter sets comprise in particular represent parameters which have an influence on the representation of the patient elements in the patient images when the images are generated. Examples of influences on representation include influences on the image values which represent the anatomical elements (such as for instance influences on a grey value which represents the anatomical element or influences on the position of an image value in a colour space which represents the anatomical element). Other examples include influences on contrast, image value range, gamut, etc.

The method in accordance with the invention in particular comprises the step of acquiring atlas data which contain information describing the general anatomical structure and in particular the representation of the general anatomical structure in an analytical image. This information is referred to as "element representation information". The element representation information describes the representation of the anatomical elements (referred to as "atlas elements") of the general anatomical structure. This representation corresponds to the representation of the anatomical elements in an image which is generated by means of an analytical device from a patient having an anatomical structure which is identical to the general anatomical structure. The influence of the generating process (for example, scanning parameters such as the type of analytical device used to generate the image and/or the measurement parameters which are set, in particular adjusted, on the analytical device and have an influence on the representation) on the representation of the one or more anatomical elements is represented by the parameter set. The atlas data, in particular a determination rule (see below) in combination with the parameter set, allow the atlas image to be determined.

The method also comprises the step of acquiring the patient data which include the patient image set and one or more of the parameter sets. Preferably, only one of the one or more parameter sets is respectively associated with one of the one or more patient images of the patient image set.

The general anatomical structure can be the anatomical structure of a complete body or the anatomical structure of only a part of the body. The general anatomical structure preferably comprises a plurality of atlas elements. The atlas elements which the general anatomical structure comprises are preferably not assigned a particular representation data set. The representation data sets can for instance describe a grey value of an atlas element. Since the atlas elements of the general anatomical structure are preferably not assigned a particular grey value, these atlas elements are also referred to here as "white atlas elements".

The anatomical structure described by the patient images can be a description of the anatomical structure of the complete body or a description of the anatomical structure of only a part of the body. The term "part" as used here can encompass either the term "complete" or the term "less than complete", i.e. only partial (within the common meaning of this term). Data (referred to as "correspondence part data") are preferably acquired which describe the part of the general anatomical structure which corresponds to the anatomical structure represented by the patient images and which is to be matched. If the entire general anatomical structure described by the atlas data is to be matched, then correspondence part data are not necessary. The (different) patient images of the patient image set preferably each describe at least approximately the same part of the anatomical structure of a patient's body. The (different) patient images of the patient image set preferably cover the description of at least one particular part of the body, i.e. at least one particular part of the body is reflected in all of the patient images of the patient image set, which is then referred to as the "common part" and comprises common anatomical elements. The matching transformation is preferably determined for at least the part of the patient images which reflect the common part of the body. The correspondence part data can comprise data (referred to as "correspondence element data") which describe the white atlas elements for which a matching transformation is to be determined. The white atlas elements for which the matching transformation is to be determined are referred to as "corresponding elements" and can be acquired for instance by receiving indication information (from a user) which indicates which white atlas elements are corresponding elements. Alternatively or additionally, the correspondence part data can be determined for example by performing a rigid transformation which rigidly matches patient images and atlas images which are respectively associated with the same parameter set, in particular without deforming the atlas elements represented in the atlas image and without deforming the patient image. Merely scaling and/or rotating the atlas images and patient images in order to achieve rigid matching is not considered to constitute deformation. In order to perform rigid matching, atlas spatial information (referred to as "coarse atlas spatial information") is preferably used which describes the general anatomical structure in less detail than the atlas spatial information used for determining the atlas images, in order to reduce the data processing load. Additionally or alternatively, the correspondence part data can describe the part (referred to as the "atlas part") of the general anatomical structure (the complete structure or only a particular part of it) which is to be used for the matching transformation and in particular can describe the part of the anatomical structure (referred to as the "patient part") represented in the at least one patient image (i.e. all of the anatomical structure or only a part of it) which is to be used for the matching transformation. At least one preliminary atlas image is then generated which represents the atlas part. Preliminary rigid matching is then performed, without deforming the atlas elements, in which the at least one preliminary atlas image and the patient part of the anatomical structure represented in the at least one patient image are matched to each other. Rigid matching in particular allows a common reference system to be established for all of the atlas images determined. The common reference system is in particular used to determine the matching transformation. This common reference system facilitates the implementation of "coupled deformation" as described below.

The data processing method in particular comprises the above-mentioned step of determining the correspondence part data, in particular the corresponding elements. The term "corresponding" as used here means in particular "anatomically the same", in particular "representing the same anatomical part" which can be understood to be a part of a patient's body which is present in a plurality of different patient's bodies and in particular belongs to the same representation classes (see below for the definition of representation classes) and/or consists of the same material and/or is located at least approximately at the same location relative to other anatomical elements and/or has a similar geometry (size and/or shape) in a plurality of different patients.

The atlas data preferably comprise atlas spatial information which spatially describes the general anatomical structure and in particular the white atlas elements. The spatial information can comprise only one set of static spatial information, i.e. spatial information which does not change over time and only provides one set of spatial properties for the general anatomical structure, or can comprise a plurality of sets of static spatial information which respectively describe the spatial properties of the general anatomical structure in different states, for instance at different points in time during for example a vital movement such as for example the breathing cycle. In particular, the spatial information describes the spatial properties, i.e. the relative position, of white atlas elements within the general anatomical structure with respect to each other and/or the geometry (size and/or shape) of the atlas elements and is preferably used to determine the spatial properties (i.e. the position and/or geometry) of the atlas elements represented in the atlas images.

A vital movement is a movement of parts of the body due to vital functions of the body, such as for example breathing and/or the heart beat. The term "vital movement" covers any kind of movement of the body which is performed unconsciously and in particular controlled by the brain stem.

The above-mentioned plurality of sets of spatial properties of the general anatomical structure can also describe different movement or posture states of the patient, such as the patient running, walking, standing or lying down. It can also cover different pathological states of a patient, such as a patient with an infection or tumour(s) in particular parts of the body, or particular states of a patient during surgery, such as a patient with an exposed skull resulting in a brain shift (which can in turn depend on the positioning of the head). The term "posture" as used here refers in particular to different positions of the extremities of the body, such as for example with the hands raised or lowered.

The element representation information describes a plurality of representation data sets, wherein "plurality" as used here means a discrete number of representation data sets (as for example described by a table) or a continuous multitude of representation data sets (as for example described by a function). Preferably, both the atlas spatial information and the element representation information are used to determine the atlas images. The representation data sets contain information describing representations of the plurality of atlas elements in the atlas images which are to be determined. In particular, the element representation information comprises information on the visual appearance of the atlas element (in an atlas image) and in particular does not include the above-mentioned spatial information. The representation information describes for example an image value (for instance, a grey value) for the respective atlas elements.

The same patient elements can be represented differently in different patient images, depending on the parameter sets. Correspondingly, the element representation information preferably does not comprise just one representation data set to be determined for respective white atlas elements but rather a plurality of representation data sets to be determined for respective white atlas elements, wherein each of the plurality of representation data sets (for each of the white atlas elements) is in particular respectively associated with one of the plurality of parameter sets. A white atlas element to which a representation data set is assigned is referred to here as a "grey atlas element", i.e. a plurality of different grey atlas elements can be determined on the basis of the white atlas elements and a plurality of different representation data sets. It is possible, on the basis of the element representation information, to determine the grey atlas elements (i.e. the representation and in particular visual appearance of a corresponding element) in an atlas image in accordance with the parameter set of a patient image which is to be matched to the atlas image. In other words, the grey atlas elements in an atlas image are determined on the basis of the parameter set of the patient image.

The patient data consist of the patient image set, i.e. one or more patient images associated with one or more parameter sets, and a description of the one or more associated parameter sets. The parameter sets associated with the patient data are preferably identical to one or more of the plurality of parameter sets of the atlas data for which the determination rule describes a determination of the representation data sets, in order to allow for a straightforward application of the determination rule. If such identity does not obtain, then the parameter set of the atlas data which is most similar to the parameter set of the patient data is preferably selected, in order to be able to apply the determination rule.

As mentioned above, the one or more atlas images are determined on the basis of the atlas data and the patient data. The one or more atlas images respectively represent at least a part of the general anatomical structure (i.e. the complete general anatomical structure or only a part of it). The respectively determined one or more atlas images represent a part of the general anatomical structure in accordance with the part of the spatial information which relates to said part of the general anatomical structure. In other words, the spatial information on the general anatomical structure, in particular the part of the spatial information which relates to atlas elements represented in the set of atlas images, is used to determine the set of atlas images. In order to determine the representation of the general anatomical structure in the set of atlas images, the representation data sets which are part of the description of the atlas data are specifically used. The determination rule described by the atlas data is applied in order to determine the representation data sets which are specifically to be used to determine the representation of the atlas elements. The determination rule refers to the parameter sets associated with the one or more patient images, i.e. the determination rule allows the representation data sets to be determined in accordance with the associated one or more parameter sets. The representation data sets preferably depend not only on the associated parameter sets but also on the corresponding elements. In short, the representation data sets are thus determined on the basis of the corresponding elements and the associated one or more parameter sets by using the determination rule described by the atlas data. The element representation information preferably describes a plurality of representation data sets (two, three or more sets) for respective white atlas elements (in particular, for each white atlas element), and the determination rule describes how one of the plurality of representation data sets is selected for a respective white atlas element in accordance with the parameter set associated with the patient image to which the atlas image is to be matched. Each selection results in a determined grey atlas element. The determination rule is for example implemented using a reference table. Alternatively, a function is used, which is in particular dependent on a number (plurality) of parameters (referred to as "scanning parameters"). A grey value relationship is for example calculated on the basis of scanning parameters, such as for example the repetition time, magnetic field strength, etc., and tissue-dependent scanning parameters such as for example the T1 relaxation time, T2 relaxation time and proton density, by using a formula. The function can thus be used to calculate the representation data set (for example, a grey value relationship) in accordance with scanning parameters. The function is in particular constituted to describe a continuous multitude of possible solutions for a representation data set (i.e. spanning the range of possible solutions), and the representation data set is calculated in accordance with the determination rule by selecting from this multitude of possible representation data sets. The determination rule in particular describes the scanning parameters which are to be selected and how they are to be used and the function in which the representation data set is to be calculated.

The method (in particular, a data processing method) in accordance with the invention also includes the step of determining a matching transformation for matching the patient image set and the atlas image set to each other. This matching transformation is referred to as an "AP transformation" (short for "atlas-patient transformation") if the atlas image is matched to the patient image. The matching transformation is determined by matching a respective image of the atlas image set and a respective image of the patient image set to each other. Matching can be performed by image fusion, which in particular uses similarity measures (see below) in order to find a matching transformation which optimally matches the respective images. The matching transformation can match one or more images of the atlas image set and one or more images of the patient image set. The respective image of the atlas image set and the respective image of the patient image set which are matched by the matching transformation are in particular associated with the same parameter set. Thus, the matching transformation is preferably determined by matching images which are associated with the same parameter set. The AP transformation in particular describes a deformation of atlas elements which is similar for all images of the atlas image set, wherein the images of the atlas image set are in particular associated with different parameter sets. This aspect is discussed in more detail below. The deformation is in particular similar if it is caused at least primarily by the deviation of the patient's anatomical structure from the general anatomical structure described by the atlas data and if the spatial properties of the patient images are similar. Any spatial distortion caused when generating the patient images is therefore preferably removed before the patient images and atlas images are matched.

In this application, the terms "image morphing" and/or "elastic fusion" are also used as an alternative to the term "image fusion", but with the same meaning.

Elastic fusion transformations (for example, image fusion transformations) are in particular constituted to enable a seamless transition from one data set (for example, a first data set such as for example a first image) to another data set (for example, a second data set such as for example a second image). The transformation is in particular constituted such that one of the first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. One or more (numerical) optimisation algorithms are preferably applied in order to find the transformation which results in an optimum degree of similarity. The degree of similarity is preferably measured by way of a measure of similarity (also referred to in this document as a "similarity measure"). The parameters of the optimisation algorithm(s) are in particular vectors of a deformation field F. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions in the one of the first and second images which is to be transformed, and the tips of the vectors lie at the corresponding voxel positions in the transformed image. A plurality of these vectors are preferably provided, for instance more than twenty or a hundred or a thousand or ten thousand, etc. There are preferably (other) constraints on the transformation (deformation), in particular in order to avoid pathological deformations (such as for instance all the voxels being shifted to the same position by the transformation). These constraints in particular include the constraint that the transformation is regular, which in particular means that a Jacobian determinant calculated from a matrix of the deformation field (in particular, the vector field) is larger than zero. The constraints also in particular include the constraint that the transformed (deformed) image is not self-intersecting and in particular that the transformed (deformed) image does not comprise faults and/or ruptures. The constraints also in particular include the constraint that if a regular grid is transformed at the same time as the image and in a corresponding manner, the grid is not allowed to interfold at any of its locations. The optimisation problem is in particular solved iteratively, in particular by means of an optimisation algorithm which is in particular a first-order optimisation algorithm, in particular a gradient descent algorithm. Other examples of optimisation algorithms include optimisation algorithms which do not use derivations, such as the downhill simplex algorithm, and algorithms which use higher-order derivatives, such as Newton-like algorithms. The optimisation algorithm preferably performs a local optimisation. If there are a plurality of local optima, then global algorithms such as simulated annealing or genetic algorithms can be used. In the case of linear optimisation problems, the simplex method can for instance be used.

In the steps of the optimisation algorithms, the voxels are in particular shifted by a magnitude in a direction, such that the degree of similarity is increased. This magnitude is preferably less than a predefined limit, for instance less than $1/10$ or $1/100$ or $1/1000$ of the diameter of the image, and in particular about equal to or less than the distance between neighbouring voxels. Due in particular to a high number of (iteration) steps, large deformations can be implemented.

The determined elastic fusion transformation (for example, a matching transformation) can in particular be used to determine a degree of similarity (also referred to as a "measure of similarity" or "similarity measure") between the first and second data sets (images). Optimum matching can for instance be defined (predetermined) as matching which results in at least a predetermined measure of similarity. To this end, the deviation between the elastic fusion transformation and an identity transformation is determined. The degree of deviation can for example be calculated by determining the difference between the determinant of the elastic fusion transformation and the identity transformation. The higher the deviation, the lower the degree of similarity. The degree of deviation can thus be used to determine a measure of similarity.

A measure of similarity can in particular be determined on the basis of a determined correlation between the first and second data sets.

The matching transformation referred to as an AP transformation preferably describes a matching transformation which matches one or more atlas images to one or more patient images, i.e. the AP transformation is preferably applied to atlas images in order to determine matched atlas images.

In an AP transformation, the spatial information (position and/or geometry) of the patient elements represented in the patient image preferably remains fixed, while the spatial information (position and/or geometry) of the atlas elements in the atlas images is changed so as to match the spatial information of the patient elements in the patient images when the AP transformation is applied. The image which results from applying the AP transformation to the atlas image is referred to as the matched atlas image. The AP transformation is preferably constituted to maintain the segmented structure of the atlas, i.e. to maintain the corresponding elements such that deformed corresponding elements are shown in the matched atlas image. Preferably, the representation of the deformed corresponding elements in the matched atlas image respectively corresponds to the representation data sets determined for the respective (unmatched) corresponding elements, i.e. the matching transformation preferably only acts on the spatial information and not on representation information described by the representation data sets, in accordance with this embodiment. In accordance with another embodiment, the representation information determined by the representation data set is adapted in view of the representation of patient elements or patient images. In accordance with yet another embodiment, at least some of the representation of at least some of the grey atlas elements is determined on the basis of the representation of patient elements, particularly if it is not possible to determine representation data sets. The patient elements are preferably identified by applying the AP transformation, which allows the patient image to be segmented into patient elements. The representation of the patient element is then determined and used in turn to determine the representation of the matched grey atlas elements of the matched atlas image.

In accordance with an alternative embodiment, the matching transformation is referred to as a PA transformation and preferably describes a matching transformation which matches one or more patient images to one or more atlas images, i.e. the spatial information (position and/or geometry) of the atlas elements represented in the atlas images remains fixed, while the spatial information (position and/or geometry) of the patient elements in the patient images is changed to match the spatial information of the atlas images in the atlas images when the PA transformation is applied. This transformation can in particular be used to improve atlas data which are to be improved (improved atlas data are referred to as "model data") by adding information from patient images to the model data. The PA transformation can be used as described in the parallel application, filed by the same applicant, entitled "Determining an Anatomical Atlas". The PA transformation corresponds to the PM transformation discussed in said parallel application and is used to improve the atlas data by means of patient data.

The step of determining the atlas image set preferably comprises the step of determining the representation data sets for the corresponding elements. The element representation information preferably describes a plurality of representation data sets for at least one (in particular, two or more) of the white atlas elements, preferably most of the white atlas elements and in particular all of the white atlas elements, i.e. the element representation information allows one of the respective plurality of representation data sets to be determined for a white atlas element in accordance with one of a respective plurality of different parameter sets by using the determination rule.

If a particular parameter set is described by the patient data for a particular patient image, then representation data sets for each of the corresponding elements are preferably determined in accordance with said particular parameter set. In particular, one of the representation data sets is selected from the plurality of representation data sets described by the element representation information for each of the corresponding elements by using the determination rule which in particular describes the representation data set which is to be selected for each of the corresponding elements in accordance with the particular parameter set described by the patient data for said particular patient image. If the patient data describe more than one parameter set and more than one patient image, then this process is preferably performed for each of the patient images. Preferably, more than one representation data set is selected from the plurality of representation data sets described by the element representation information in accordance with the determination rule and the plurality of parameter sets described by the patient data for more than one patient image, in order to allow more than one atlas image to be determined, i.e. for each of the corresponding elements. For each of the corresponding elements, the number of selected representation data sets preferably corresponds to the number of patient image sets if there is a different representation of the atlas element for each of the parameter sets described by the patient data. The determination rule preferably refers to the same parameter set for all of the corresponding elements of an atlas image, i.e. the parameter set of the patient image to which the atlas image is to be matched (or vice versa). Thus, an atlas image is preferably associated with only one parameter set.

The determination rule in particular comprises an assignment rule for respectively assigning one representation data set to one corresponding element for each different parameter set. The assigned representation data set describes the representation of the corresponding element in the atlas image associated with one of the different parameter sets. The assignment rule preferably depends on the parameter set which is associated with the patient image which includes the patient element to which the corresponding element is to be matched.

In accordance with one embodiment, the determination rule comprises assignment rules for (all of) the respective white atlas elements, so that there is an assignment rule for each of the white atlas elements to be matched, i.e. for each of the corresponding elements. In accordance with preferred embodiments, the assignment rule is simplified by not providing an assignment rule for each of the atlas elements but rather for classes of atlas elements, referred to as representation classes (or also "tissue classes"), and preferably assigning (each of) the respective atlas elements to one of the representation classes. This reduces the processing load of the data processing method. For each of the white atlas elements belonging to the same respective representation class, the same representation data set is preferably determined for each of the respective parameter sets. In other words, different grey atlas elements belonging to the same representation class are represented in an atlas image in accordance with the same representation data set, irrespective of the individual parameter set associated with the atlas image which includes the different grey atlas elements. Further details with respect to representation classes are given below.

The representation (representation properties) of the corresponding elements in the one or more atlas images is/are determined on the basis of the determined representation data sets. Each of the corresponding elements represented in the one or more atlas images is in particular represented in accordance with the assigned representation data sets. All the corresponding elements of a respective atlas image are preferably associated with the same parameter set.

The representation data sets can represent rules for defining absolute values of representation, such as an absolute image value (for example, an absolute grey value or an exact position in a colour space) which is in particular used for the whole space occupied by a grey atlas element. The representation data sets can also describe relative rules for representation (in particular, for the representation of image values), such as for instance that one particular atlas element should be represented with a lower grey value than another particular atlas element or that a colour value is shifted in a particular direction from one atlas element to another. The parameter sets can also represent incomplete information (at least for some of the corresponding elements) which does not allow a representation data set to be determined directly for all of the corresponding elements (for example by simply using a reference table). The parameter set can for example be incomplete in that it is not known whether a contrast agent was injected into the patient before the patient image was generated or not. The representation of a corresponding element which can be influenced in terms of its representation by a contrast agent will then be uncertain. Flexibility in determining the representation of one or more of the corresponding elements is then desirable. This is preferably achieved by performing a first matching process (using image fusion) and comparing the matched atlas images with the patient images. The first matching process relies in particular on spatial properties only, in particular with respect to the corresponding elements for which a representation data set has not yet been determined. This first matching process in particular allows the patient image to be segmented into patient elements. On the basis of the comparison, the representation of the corresponding elements is changed so as to be closer to the representation of the corresponding patient elements in the patient images. In the next step, the matching transformation is correspondingly adapted such that applying the matching transformation to the atlas images (i.e. a second matching process) results in matched atlas images in which the representation of corresponding elements is more similar to the representation of the corresponding patient elements in the patient images than it was after the first matching process but before the second matching process. Thus, the determination rule preferably uses information on the representation of the patient elements in the patient images in order to determine the representation of the matching elements. This information is referred to as patient image representation data, which in particular describe the image values which represent the patient elements.

The term "similar" as used here generally covers the two meanings of "similar but not identical" and "similar and identical", i.e. the term "similar" in particular also covers the term "identical". The above-mentioned similarity measure can be used to quantify the term "similar", and a predetermined threshold for the similarity measure can be applied in order to differentiate between what is similar and what is not similar.

As mentioned above, the patient images can be associated with different parameter sets, wherein anatomical elements of the patient represented by one or more of the patient elements in the patient images associated with different parameters are in particular identical. If, for example, a CT image and an MR image of a patient element (for example, the lung) are provided, then a matching transformation which deforms an atlas element to match a patient element associated with a parameter set and a matching transformation which transforms the atlas element to match the patient element represented in another patient image associated with another parameter set will perform a similar spatial deformation if there is no geometric distortion incurred by the analytical devices or if the incurred distortion is similar in each case. The matching transformation is preferably constituted to match one of the atlas images to one of the patient images associated with one of the parameter sets and another of the atlas images with another of the patient images associated with another of the parameter sets. Determining the part of the matching transformation which matches one of the atlas images and one of the patient images, both of which are associated with the same parameter set, to each other preferably involves taking into account information on another part of the matching transformation which matches another of the atlas images and another of the patient images, which are associated with another of the associated parameter sets, to each other. Thus, information resulting from different matching processes (relating to different parameter sets) is used reciprocally in order to improve the quality of matching. The reciprocally used information is in particular spatial information. Preferably, a spatial correlation between patient images associated with different parameter sets is determined before this reciprocal information is used. Atlas images and patient images are for example rigidly matched to each other, in particular in order to establish a common spatial reference system for all the patient images, in particular so that deformation vectors relating to different matching processes can be determined. As mentioned above, the matching transformation preferably performs different matching processes, i.e. matches atlas images and patient images associated with different parameter sets, wherein the images comprises common patient elements (of the same patient).

The matching transformation (in particular, the AP transformation) is generally determined in such a way that (first) spatial information on matching one of the atlas images (a first atlas image) and one of the patient images (a first patient image) to each other (in particular, information on matching one of the atlas images to one of the patient images) is used to determine how another of the atlas images (a second atlas image) and another of the patient images (a second patient image) are matched to each other. The former matching process is preferably described by a first part of the matching transformation, while the latter matching process is preferably described by a second part of the matching transformation. The first atlas image and first patient image which are subjected to the former (first) matching process are associated with a first parameter set, while the second atlas image and second patient image which are subjected to the latter (second) matching process are associated with a second (different) parameter set. Thus, the first spatial information is used as a basis for determining the second part of the matching transformation (in particular, the second part of the AP transformation) which matches another of the atlas images and another of the patient images to each other, i.e. one part of the matching transformation which relates to one of the parameter sets uses information (in particular, spatial information) from another part of the matching transformation which performs matching with respect to another parameter set.

As mentioned above, the spatial deformation represents an example of the information used in this way. The information can in particular be used reciprocally, i.e. reciprocal information is used. In order to apply the reciprocal information, the matching transformation is varied on the basis of the reciprocal information, and the quality of the matching transformation for different variations is determined. Preferably, the variation which results in the highest-quality matching transformation is selected. In order to determine the quality of the matching transformation, the quality of a matching process between a patient image and an atlas image is in particular determined. The matching quality can be determined on the basis of the degree of similarity (for example, quantified by the similarity measure) between the images after matching has been performed. If the matching transformation is determined by applying the same spatial changes (change in position and/or geometry) to one of the first atlas image and first patient image (in particular the first atlas image in the case of AP transformations) and one of the second atlas image and second patient image (in particular the second atlas image in the case of AP transformations), then the deformation can be varied by varying the transformation, and the kind of transformation which is determined as the matching transformation is the one which on average (for example, by averaging a similarity measure determined for a first AP sub-transformation APT1 and a similarity measure determined for a second AP sub-transformation) results in the greatest similarity between the respective atlas images and the respective patient images.

In accordance with one embodiment, the matching transformation comprises parts which are distinct matching sub-transformations. The matching sub-transformations are preferably coupled, since spatial information—in particular, properties of the matching sub-transformations (such as the deformations determined by the matching sub-transformation)—have an influence on each other. The respective matching sub-transformations respectively match the atlas images associated with a respective associated parameter set and a respective patient image associated with the same respective associated parameter set, i.e. each matching sub-transformation is directed to a matching process relating to one of the parameter sets. The matching sub-transformations are in particular AP sub-transformations which respectively match one atlas image to one patient image. The matching sub-transformations are in particular coupled in that they each influence the determination of the other. One of the matching sub-transformations is in particular determined on the basis of determining another of the matching sub-transformations. This coupling is in particular based on a spatial correlation between atlas images and patient images associated with different parameter sets. As mentioned above, the correlation can in particular be established by means of rigid transformations applied with respect to the different parameter sets. The spatial correlation between the atlas images in particular is preferably known, since they represent the same (part of) the general anatomical structure, i.e. the same spatial information. The representation of the structure (in particular its visual appearance) in the atlas images can differ in accordance with the associated parameter sets.

As mentioned above, representation classes are preferably used to classify the atlas elements. Each atlas element is preferably assigned to one of the representation classes. The representation classes define the representation of the atlas elements for different parameter sets. The atlas elements are preferably assigned to the representation classes surjectively. The determination rule preferably uses the assignment between atlas elements and representation classes to describe an assignment between atlas elements and representation data sets. This advantageously simplifies the assigning process, since a number of in particular different atlas elements (such as for example one, two or more atlas elements, in particular different atlas elements) can preferably be assigned to the same representation class. Preferably, each of the representation data sets describes the representation of one particular atlas element which is associated with one parameter set. If particular atlas elements belong to the same representation class, then the same representation data set is determined for all of these particular atlas elements by the determination rule, providing they are associated with the same parameter set. If one or more representation data sets is/are respectively associated with one or more parameter sets for a particular representation class, then the one or more representation data sets represent a subset of a plurality of representation data sets. The subset is defined within the particular representation class and is selected by the determination rule for an atlas element belonging to said particular representation class. Thus, a representation class represents a subset of the representation data sets. The determination rule assigns a particular representation data set of the subset to an atlas element belonging to the representation class in accordance with the parameter set. In other words, the respective representation classes represent respective subsets of the plurality of representation data sets, and for each representation class, there is a characteristic bijective assignment between the representation data sets of the subset and the parameter sets, i.e. for each representation class, the determination rule assigns one representation data set (of the subset) to an atlas element belonging to the representation class, wherein the assignment is made in accordance with the parameter set associated with the patient image comprising the patient element to which the atlas element is to be matched.

As mentioned above, the representation data sets describe the representation (also referred to as the "representation property"), in particular the visual appearance, of anatomical elements in an atlas image. In particular, the representation data set can for example describe (as an example of a representation property) image values, in particular a single image value for a particular anatomical element or a single average value for the region (in particular, area) occupied by the anatomical element. The image value can for example be a grey value, an intensity value, a colour value, a value in a colour space, etc. The representation data set can also describe (as an example of a representation property) a lower limit and/or upper limit of the image values, for instance a range of grey values or a range in the gamut of the colour space for a particular anatomical element (in particular, for each of the representation classes). The representation data set in particular describes (as an example of a representation property) a relationship between image values of different anatomical elements, for instance that a grey value is higher in one anatomical element than in another anatomical element. Any such description refers of course to a particular parameter set. With respect to another parameter set, the relationship may be different. The relationship can of course also be in the colour space and consist for instance of the fact that the intensity is higher for one anatomical element than for another or that there is a shift in the colour space in a particular direction if the image value of one anatomical element is compared with the image value of another anatomical element. Aside from the aforementioned average of image values for the anatomical elements (associated with particular parameter sets), a standard deviation from the average image values can be described by the representation data sets. Structures of modulations of the image values can also be described (as an example of a representation property) for the anatomical elements by the representation data sets. Spatial modulations of image value variations within the anatomical element can for example be described (for instance by means of DCT coefficients). Characteristics of transitions between representations of different anatomical elements can also be described (as an example of a representation property). The transition from a bone structure to a soft tissue structure is for example different in an x-ray image as compared to an MRT image. In particular, the representation property does not comprise spatial information, hence the representation data set in particular does not describe spatial information. The representation property is also referred to as "representation information".

The above-mentioned representation classes are in particular substance classes (also referred to as "tissue classes"), since anatomical elements which are of a similar substance can be represented by the same subset of representation data sets, wherein each member of the subset is respectively assigned to one of the parameter sets. An anatomical element consisting mainly of a particular substance (for instance, fat or bone) will for example have the same representation (in particular, visual appearance), irrespective of where the anatomical element is located in the patient's body. Thus, in accordance with one embodiment, information on the substance of an anatomical element is used to assign the anatomical element to one of the representation classes.

As mentioned above, the atlas data comprise atlas spatial information on a description of spatial information (i.e. position and/or geometry) for the general anatomical structure. In accordance with one embodiment, the spatial information is static, i.e. the position and/or geometry of the general anatomical structure is fixed for all elements. In accordance with a preferred embodiment, the spatial information is flexible, i.e. the position and/or geometry of one or more of the atlas elements is flexible. The term "flexible" as used here means in particular that a variation in the position and/or geometry is allowed in order to improve the quality of the matching process. As mentioned above, the matching quality can be measured by determining the degree of similarity (by means of a similarity measure) between the element (for example, an atlas element) which is subjected to the matching transformation and the element (for example, a patient element) to which the transformed element is to be matched.

There are in particular anatomical elements which can significantly vary in terms of their position from patient to patient. The flexibility information can accordingly include a statistical probability for different positions and/or geometries of the anatomical element. The position of the kidney can for example vary from patient to patient. For the purposes of this document, an organ is not generally an anatomical element but can comprise different anatomical elements, since an organ can consist of regions occupied by different types of substances. Conversely, an anatomical element may be larger than an organ. The brain stem, for example, is only part of the white matter but is not clearly separated from other parts of the white matter. In accordance with one embodiment, organs which cannot be clearly differentiated from other organs, such as the brain stem, are identified as a substructure within an anatomical element. Preferably, an anatomical element consists at least predominantly of one or more substances which manifest themselves through the same representation property in analytical images associated with different parameter sets, i.e. the one or more substances belong to the same representation class.

The above-mentioned flexibility information which can be part of the atlas spatial information is in particular used as a constraint when determining the matching transformation. The anatomical variability of the position of anatomical elements as mentioned above represents one reason for the use of flexibility information. Another reason is changes in the position of anatomical elements due to intentional changes in position brought about by the patient or a user (such as for example medical staff). The arms and legs of a patient can for example adopt different positions with respect to the patient's torso. The variability of these possible positions, in particular due to the variability of the extremities of the patient's body, can also form a basis for the flexibility information. Another reason for using flexibility information can be the different positions of organs (and therefore anatomical elements) due to the different sizes of the lung(s) during a breathing cycle or due to the heart beat or other, unintentional movements.

Anatomical variability can also be due to a pathological change in the patient's body. The development of a tumour can for example shift parts of the brain.

The flexibility information can in particular also comprise a constraint with respect to positions and positional changes such as rotations. A rotation of one vertebra with respect to another by more than 180° is for example anatomically impossible and can accordingly be excluded by means of the flexibility information.

The expression "acquiring data" encompasses in particular (within the framework of a data processing method) the scenario in which the data are determined by the data processing method or program. Determining data in particular encompasses measuring physical quantities and transforming the measured values into data, in particular digital data, and/or computing the data by means of a computer and in particular within the method of the invention. The meaning of "acquiring data" also in particular encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. In particular, the acquiring step does not involve an invasive step which would represent a substantial physical interference with the body requiring professional medical expertise to be carried out and entailing a substantial health risk even when carried out with the required professional care and expertise. Acquiring—in particular, determining—data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information".

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a nonvolatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The method in accordance with the invention is preferably at least partly executed by a computer, i.e. all the steps or merely some of the steps (i.e. less than the total number of steps) of the method in accordance with the invention can be executed by a computer.

The object stated at the beginning is achieved by the subject-matter of any of the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically sensible and feasible. A feature of one embodiment which is functionally identical or similar to a feature of another embodiment can in particular replace said latter feature. A feature of one embodiment which supplements a function of another embodiment can in particular be added to said other embodiment.

As mentioned above, the method described here can also be applied if the patient images describe an anatomical structure which exhibits pathological changes. This can be handled using the above-described flexibility information. In accordance with another embodiment described in the following, parameters referred to as "patho parameters" are used to determine and in particular select information on the general anatomical structure which fits the anatomical structure of the patient which exhibits pathological changes. More specifically, the patho parameter specifies and in particular classifies the pathological changes to the anatomical structure, i.e. the general anatomical structure as compared to a healthy patient and the anatomical structure of the patient as compared to a healthy patient. The patho parameter in particular specifies the anatomical structure in accordance with a medical classification system such as the TNM Classification of Malignant Tumours. The data processing method is preferably embodied by the following method:

A data processing method for determining a matching transformation for matching an image of an anatomical body structure of a patient, referred to as a patient image, and an image of a general anatomical structure, referred to as an atlas image, wherein both the anatomical body structure of the patient and the general anatomical structure exhibit pathological changes and the patient image is associated with one of a plurality of different parameters which are referred to as patho parameters and specify the pathological changes in accordance with a classification, the method comprising the following steps performed by a computer:
    acquiring atlas data which contain information on a description of a plurality of images of the general anatomical structure for a plurality of patho parameters and in particular spatial meta information on the pathological changes; and
    acquiring patient data, comprising the sub-steps of
        acquiring the patient image, and
        acquiring the patho parameter associated with the patient image set;
    determining, on the basis of the atlas data and the patient data, the atlas image which represents at least a part of the general anatomical structure which exhibits pathological changes in accordance with the patho parameter; and determining the matching transformation which matches the atlas image and the patient image and in particular matches the spatial meta information to the patient image.

The above-described method represents an alternative and independent method of an alternative and independent invention. The above-described method is preferably combined with the method described in claim 1 or any of dependent claims 2 to 13. As described above, atlas data are acquired which contain information on a description of a plurality of images of the general anatomical structure for a plurality of patho parameters, i.e. each image of the plurality of images specifies a particular general anatomical structure which exhibits a particular pathological change. The information on the description is in particular the image (atlas image) of the general anatomical structure which is associated with the particular patho parameter and/or can be spatial information on the general anatomic structure as described above which is associated with the particular patho parameter and/or can be element representation information as described above which is associated with the particular patho parameter. In accordance with another step of this alternative method, the patient data are acquired. The patient data comprise at least one patient image which is associated with a particular patho parameter. This allows the information on the description of one of the plurality of images of the general anatomical structure, which exhibits the pathological changes specified by the particular patho parameter, to be determined. If the information on the description is an atlas image, then the atlas image is determined by selecting the atlas image which is associated with the particular patho parameter. In a following step, the matching transformation which matches the atlas image and the patient image to each other and in particular matches the atlas image to the patient image (both of which are associated with the same patho parameter) is determined.

As mentioned above, the alternative method can be combined with the method described above. In particular, the atlas data describe the spatial information on the general anatomical structure for a plurality of different patho parameters. The spatial information of atlas elements can in particular vary in accordance with the patho parameters, for example due to deformation caused by tumours. The element representation information also varies in accordance with the patho parameters. In particular, a spatial distribution of representation information within the different anatomical elements (atlas elements) varies in accordance with the patho parameters. The spatial distribution of the representation information in particular represents an average spatial distribution of pathological changes associated with the respective patho parameter. In addition to the element representation information or as an alternative to the element representation information, meta data referred to as patho meta data can be acquired. The patho meta data describe meta information on pathological changes to the general anatomical structure associated with a particular patho parameter. This meta information can in particular be a statistical probability distribution for the presence of pathological changes within the respective atlas elements (in particular, a spatial statistical distribution of such a probability which depends on positions or sub-regions within the atlas element) and/or can be information on an average geometry of distinct pathological changes (distinct tumours) and/or can be information on an average number of distinct pathological changes and variations of said number. In particular, the matching transformation can transform (and in particular deform) the spatial statistical probability distribution associated with the atlas image onto the patient image by using the matching transformation, i.e. the spatial statistical probability distribution of pathological changes represents spatial meta information on the pathological changes which is matched to the patient image. The spatial statistical distribution is an example of spatial meta information.

If, for example, the atlas data only contain spatial information on the general anatomical structure and the spatial meta information, then the spatial properties of the white atlas elements to be matched to the patient image are determined on the basis of the patho parameter, and the spatial meta information for the white atlas elements is determined on the basis of the patho parameter. The spatial statistical probability distribution can for instance be described by a two-dimensional or three-dimensional contour line model. This model is deformed in accordance with the deformation of the spatial properties of the atlas elements when the atlas element (the white atlas element combined with the spatial meta information) is matched to the patient image.

Additional features of the invention are disclosed in the following description of embodiments. Different features of different embodiments can be combined.

FIGS. 3A to 3D show the steps of the data processing method discussed in the present matching section (the matching method).

Figure 1A:
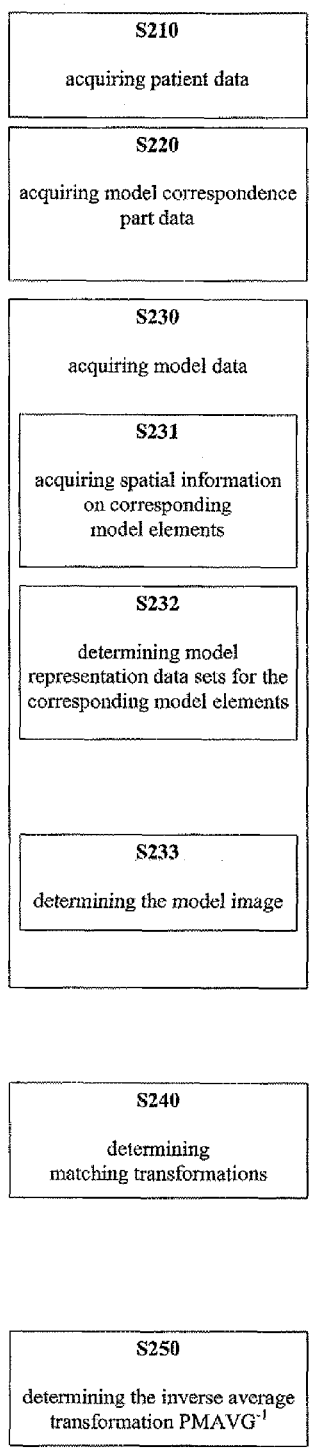
Figure 1A:
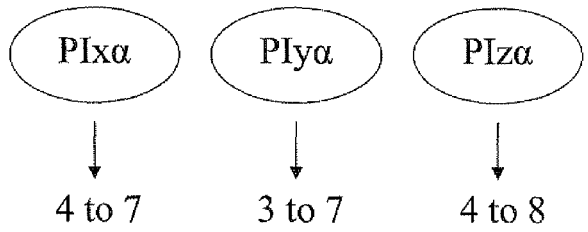
Figure 1A:
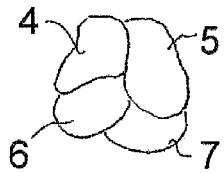
Figure 1A:
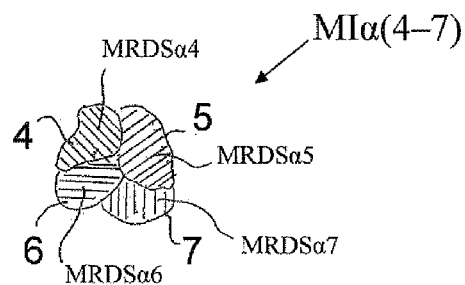
Figure 1A:
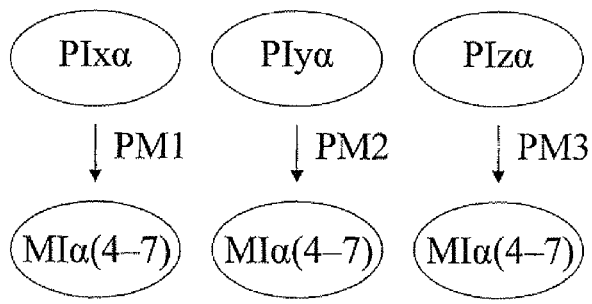
Figure 1B:
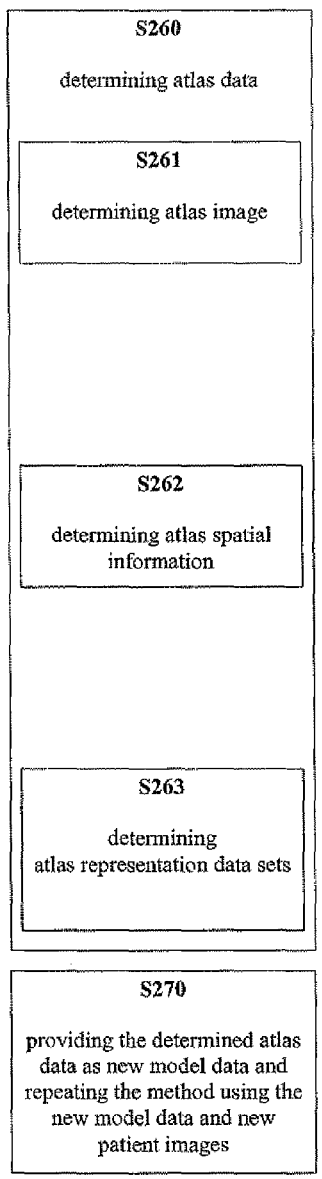
Figure 1B:
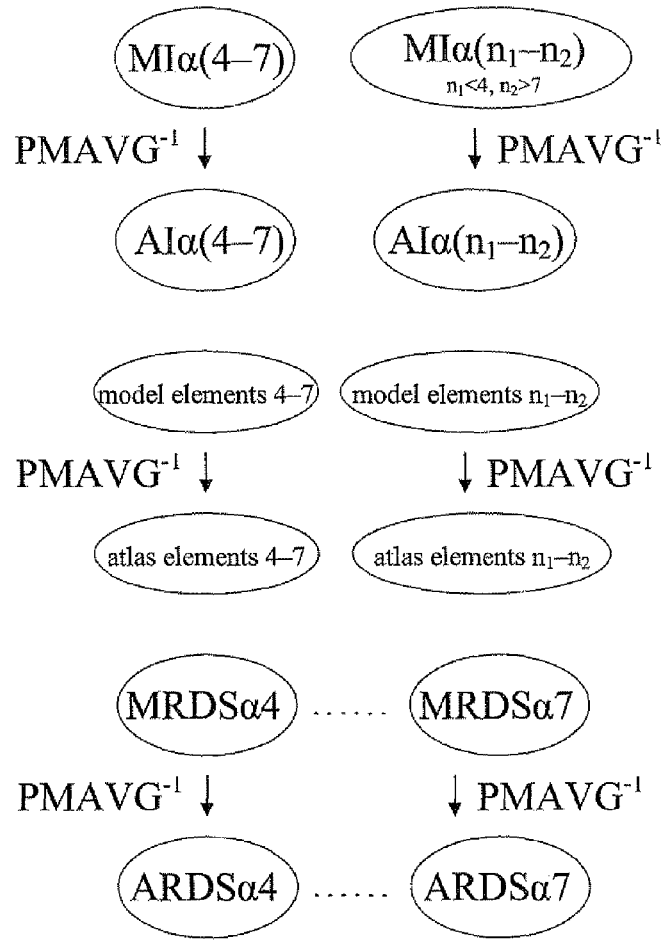
Figure 1C:
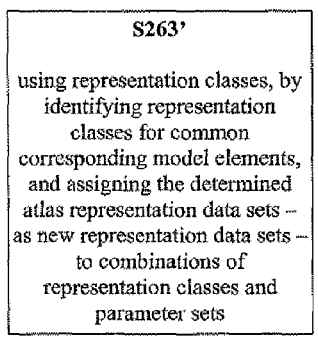
Figure 1C:
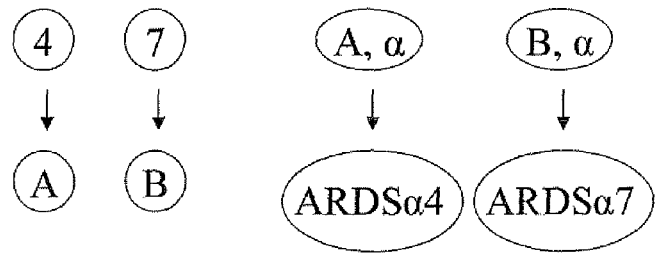

FIGS. 3A to 3D show the steps of an embodiment of the data processing method discussed in the present matching section (the matching method). The individual steps and/or sub-steps of this embodiment are described on the left-hand side in FIGS. 3A to 3D. Explanatory drawings pertaining to the individual steps are respectively shown on the right-hand side in FIGS. 3A to 3D, i.e. each of the explanatory drawings refers to the method step directly to the left of it.

In a first step S110, atlas spatial information is acquired. The atlas spatial information describes the geometry of the atlas elements and their relative position. The accompanying explanatory drawing illustrates the geometry and relative position in two-dimensional space of seven atlas elements 1 to 7. The atlas is preferably three-dimensional.

Further below in FIG. 3A, Step S120 begins with the sub-step S121. In the course of Step S120, representation information is acquired. Acquiring the representation information preferably involves acquiring an assignment between atlas elements and representation classes (Sub-step S121). The use of representation classes allows the data processing load to be reduced and in particular reflects the physical property of an anatomical body that different anatomical elements can consist of the same substance (tissue). As shown in Table 1 to the right of Sub-step S121, each of the atlas elements 1 to 7 is assigned to one of the representation classes A, B, C and D. The atlas element 1 is for example assigned to the representation class A, the atlas element 5 is assigned to the representation class D, and the atlas element 7 is assigned to the representation class B. Since the atlas element 2 is also assigned to the representation class B, assignment is preferably surjective, i.e. different atlas elements can be assigned to the same representation class. This reduces the processing load.

Figure 3A:
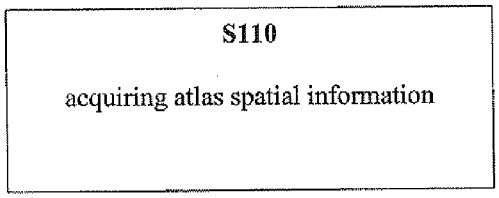
Figure 3A:
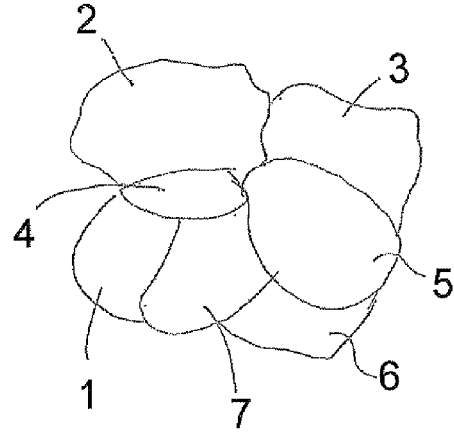
Figure 3A:
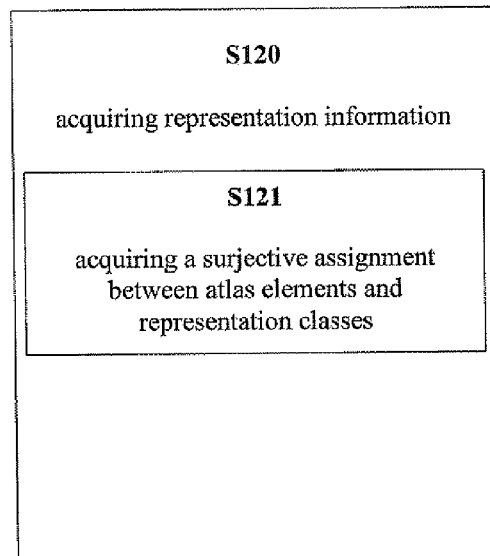
Figure 3A:
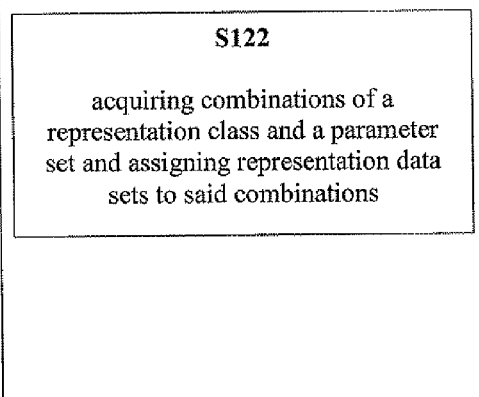

Sub-step S122 is shown at the bottom left of FIG. 3A. In this sub-step, representation data sets are assigned to combinations of a representation class and a parameter set. The representation data set a is for example assigned to a combination of the representation class A and the parameter set α. Preferably, all or at least most of the possible combinations of representation classes and parameter sets are assigned one of the representation data sets. An example of such an assignment is shown in Table 2. Thus, for example, the atlas element 5 is assigned to the representation class D, as shown in Table 1, and the representation class D is represented in accordance with the representation data set c if the parameter set is α and/or is represented in accordance with the representation data set d if the parameter set is β and/or is represented in accordance with the representation data set i if the parameter set is γ. This reflects the fact that anatomical elements can be represented differently, depending on the parameter set (for example, the image modality).

Sub-step S123 is shown at the top left of FIG. 3B. In Sub-step S123, the description of the representation data set is acquired, i.e. representation information which in particular describes the visual appearance of an anatomical element (except for spatial information such as geometry and/or size) is described. In the given example, the representation data set c features horizontal, parallel lines as an example of a visual appearance. The lines shown in the right-hand column of Table 3 are intended to represent for example the different grey values in an anatomical image generated by an analytical device. The letters in the left-hand column of Table 3 can for instance represent particular grey values.

In addition to the aforementioned sub-steps S121, S122 and S123, an additional sub-step S124 within Step S120 is also shown, in which a determination rule is acquired. It should be noted at this juncture that the sequence of method steps shown in FIGS. 3A and 3B is not obligatory.

Sub-step S124 relates to the step of acquiring the determination rule. In accordance with one embodiment, the determination rule describes how a representation class is selected for an atlas element using a table which assigns atlas elements to respective representation classes. When applying the rule, the corresponding elements have preferably already been identified, such that the representation classes assigned to the corresponding elements are determined in a first sub-step of the determination rule (using Table 1). In accordance with a second part of the determination rule, the representation class selected for the corresponding element and the parameter set associated with the patient image (to which the atlas image is to be matched) are used to determine the representation data set (using Table 2). The representation data sets for the corresponding elements are thus determined in the second sub-step of the determination rule.

A third part of the determination rule stipulates that the representation information corresponding to the representation data set can be acquired for instance by using a table in order to allow particular representation information to be assigned to the respective corresponding elements when the determination rule is to be applied (see Sub-step S143).

In short, the determination rule in particular regulates the way in which the representation information for the atlas elements is to be determined when the corresponding elements and the parameter sets are known.

Figure 3C:
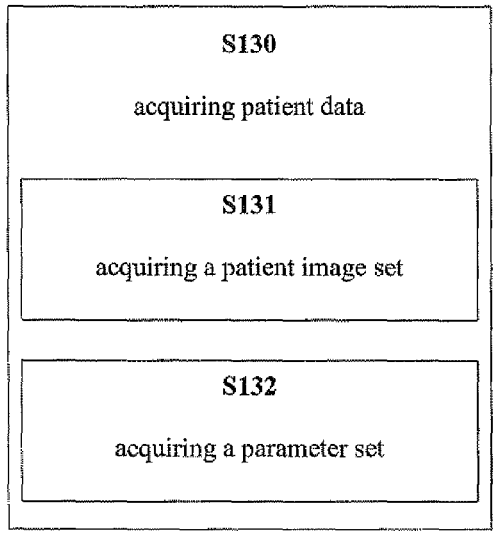
Figure 3C:
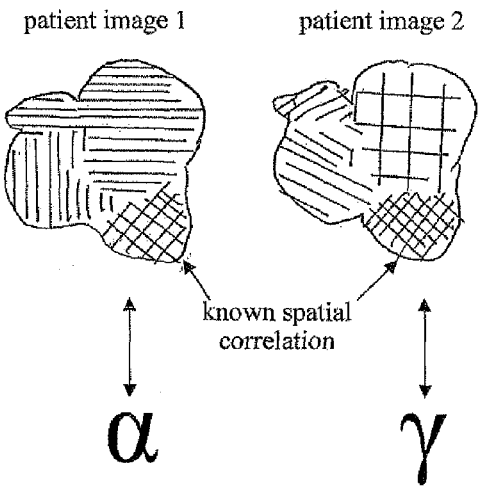
Figure 3C:
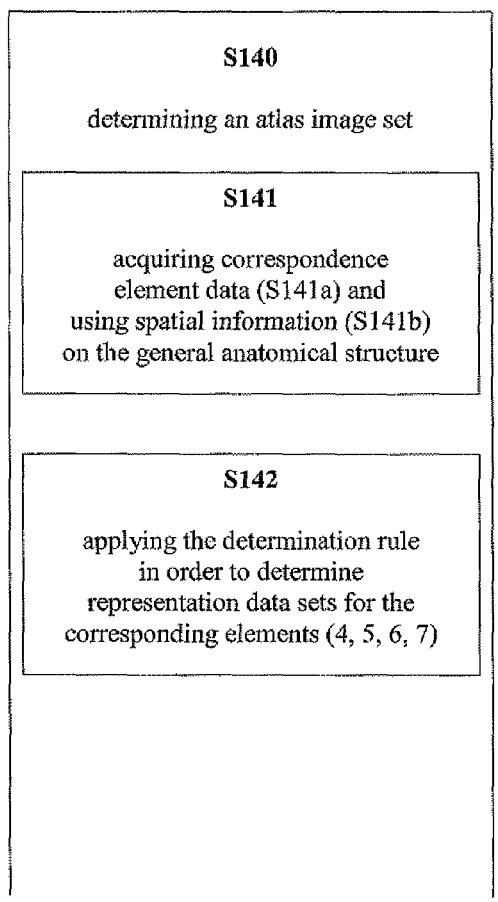
Figure 3C:
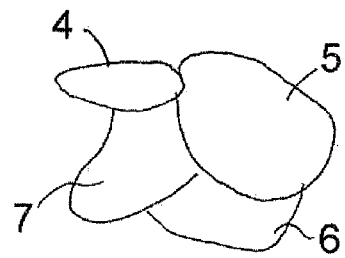
Figure 3D:
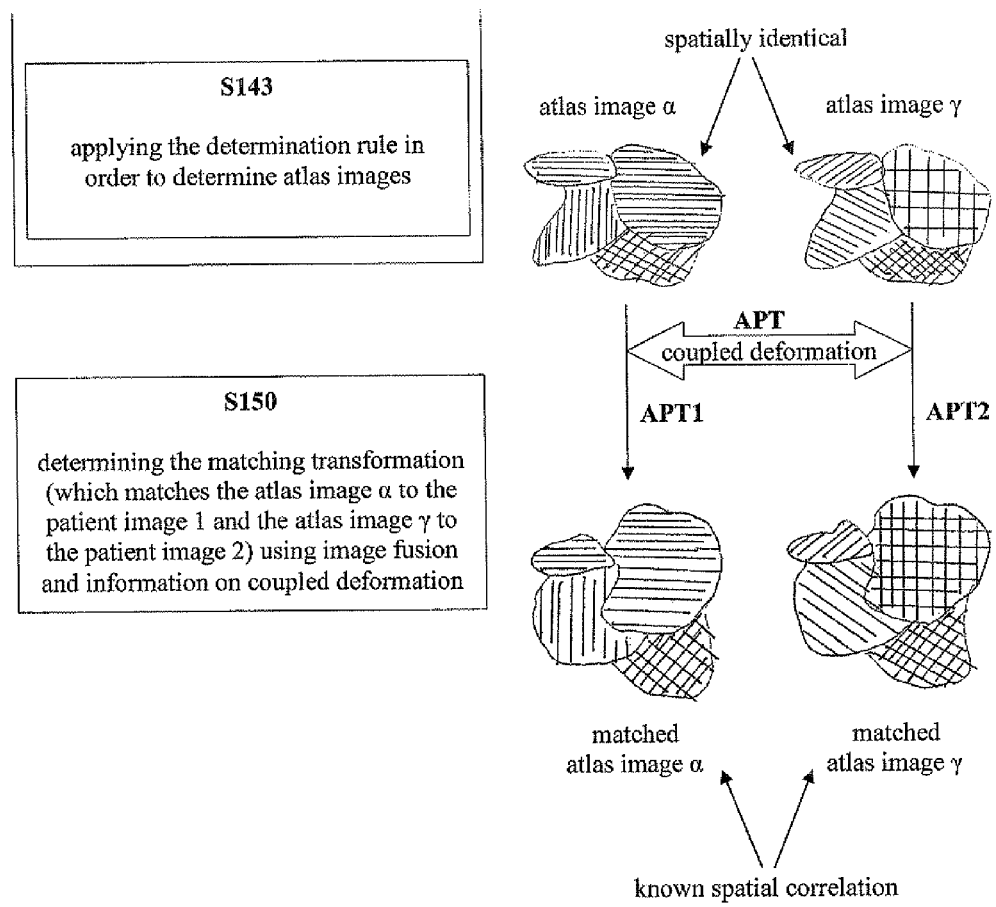

The step of acquiring patient data is shown at the top left of FIG. 3C. This step S130 comprises two sub-steps S131 and S132. The first sub-step S131 relates to acquiring a patient image set. In the example given at the top right of FIG. 3C, the patient image set comprises a patient image 1 and a patient image 2. A parameter set is respectively assigned to each of the patient images, i.e. the parameter set α is assigned to patient image 1, and the parameter set γ is assigned to patient image 2.

The patient data preferably also comprise information on the spatial correlation between the patient images in the patient image set. The spatial correlation is in particular known. It is for example known that the spatial information is identical, i.e. the geometry and size of the anatomical elements shown in the patient image and their relative position is identical, or that the deviations from such identity are negligible. In accordance with an alternative embodiment, the patient images are not identical, but a spatial transformation is known which allows the spatial information of one patient image to be transformed into the spatial information of another patient image. One of the analytical devices may for example generate a known spatial distortion which can be described by a spatial transformation. Even if the spatial distortion is not known, spatial distortions usually have a low spatial frequency, such that it is preferably assumed that high spatial frequency information included in the patient images is identical.

In addition to the patient image sets acquired in Sub-step S131, parameter sets are preferably also acquired in Sub-step S132. In the example given to the right of Sub-step S132, the parameter set α is acquired for the patient image 1, and the parameter set γ is acquired for the patient image 2.

The aforementioned data acquisition steps S110, S120 and S130 can be performed in parallel or sequentially. The atlas image set is then determined in Step S140.

Step S140 preferably comprises the sub-step S141 in which the correspondence element data are acquired. The correspondence element data describe the atlas element which corresponds to the structure shown in the patient images of the patient image set, i.e. the atlas elements which have corresponding patient elements in the patient images and are to be the subject of a matching transformation. In the example given, the correspondence element data describe the atlas elements 4, 5, 6 and 7 as being corresponding elements.

Figure 2:
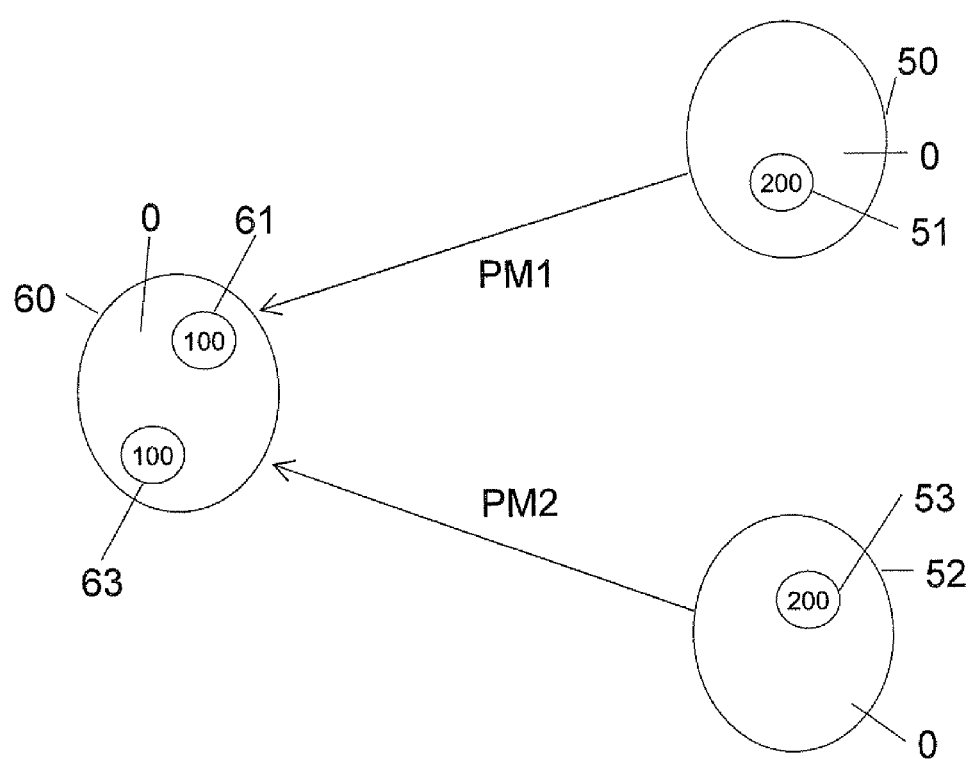

In another part of S140, namely Sub-steps S142 and S143, the determination rule is applied in order to determine the atlas images. To this end, the representation data sets are determined for each of the corresponding elements 4, 5, 6 and 7 and for each of the atlas images α and γ by referring to Tables 1 and 2, i.e. Table 1 indicates the representation class C for the atlas image α and the corresponding element 4, and Table 2 indicates the representation data set c for the representation class C and the parameter set α. As can be seen from the table at the bottom right of FIG. 2C, the corresponding elements 4 and 5 have the same representation data set in the atlas image α but different representation data sets in the atlas image γ, i.e. the atlas elements 4 and 5 can only be differentiated in the atlas image γ. As can also be seen from the patient images 1 and 2, only patient image 2 shows different grey values between the top left and top right of the image.

Since the atlas images α and γ are generated from the same atlas, the spatial information (geometry and size) of the atlas image α is identical to the spatial information of the atlas image γ.

In a subsequent step S150, the matching transformation is determined. In the example shown in FIG. 3D, the matching transformation is an AP transformation which matches the atlas image α to the patient image 1 and the atlas image γ to the patient image 2. The spatial correlation between the patient image 1 and the patient image 2 is preferably known. In the example given, the spatial information of patient images 1 and 2 is identical, i.e. the atlas images α and γ undergo the same deformation. This is an example of coupled deformation. As mentioned above, the corresponding elements 4 and 5 have the same representation data set for α but different representation data sets for γ. This allows the corresponding elements 4 and 5 to be segmented even for the matched atlas image α, since the deformation is coupled and the spatial information of the matched corresponding element 5 in the matched atlas image α is therefore the same as the spatial information of the matched corresponding element 5 in the matched atlas image γ, i.e. the spatial information of bone structures in a CT image can for example be used in order to identify the corresponding structures in an MR image, while conversely, the spatial information on anatomical elements consisting of soft tissue as provided by MR images can be used to determine the corresponding matched atlas elements in a matched atlas image representing a CT image.

The aforementioned AP transformations (APT1 and APT2) can be determined simultaneously or iteratively. If iteratively determined, a first trial APT1 is for example determined which results in a best match between the atlas image α and the patient image 1. Information on deformation is extracted from the first trial APT1. The deformation from the first trial APT1 is then applied when matching the atlas image γ to the patient image 2 by means of a first trial APT2. The first trial APT2 is then varied by varying the deformation, in particular within a predetermined range. If a varied deformation results in a better match, then this varied deformation is used to determine a second trial APT1. The second trial APT1 uses the varied deformation to match the atlas image α to the patient image 1. Again, the second trial APT1 can be varied by varying the deformation, in particular within a predetermined range, in order to determine another modified deformation which can then in turn be applied in order to determine a second trial APT2. This process can be repeated until varying the deformation no longer improves the averaged matching quality for APT1 and APT2. Instead of the sequential determination approach described above, a simultaneous determination approach is also possible and represents another preferred embodiment.

In accordance with one embodiment, the deformations described by APT1 and APT2 are described by using deformation vectors and establishing a common reference system for APT1 and APT2 (for example, by way of a preliminary rigid transformation as mentioned above). In accordance with one embodiment, the deformation vectors determined for APT1 and APT2 are added in a first iterative step of determining the matching transformation, i.e. a first deformation vector for describing the deformation of a part of the atlas image α by APT1 and a second deformation vector for describing the deformation of a part of the atlas image γ by APT2 are for example provided. These deformation vectors for the atlas image α and the atlas image γ preferably originate at the same spatial point or region in a common reference system. Usually, fusion algorithms result in a deformation vector of 0 if no clear information on deformation can be found. If the deformation can only be reliably determined from one of the transformations APT1 and APT2, then adding the deformation vectors means that the determination is primarily based on the part of the matching transformation which provides the most information. The deformation described by the matching transformation is therefore preferably weighted in accordance with the amount of image information (described for instance by image energy or contrast) available in at least one of the patient image and atlas image, preferably the patient image. The matching transformation is preferably determined for all or at least most of the parts of the images in the way described above, by determining a plurality of deformation vectors for each transformation.

Figure 4:
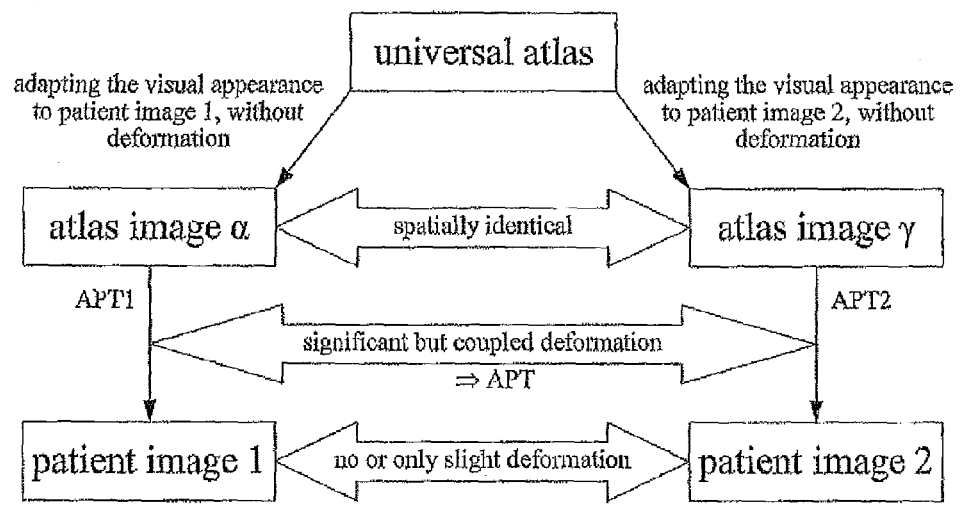
FIG. 4 shows a flow diagram which illustrates and explains correlated matching.

FIG. 4 shows a flow diagram which illustrates and explains correlated matching.

The universal atlas describes the general anatomical structure and is used to determine an atlas image α and an atlas image γ. The atlas images α and γ are spatially identical, but their representation information is respectively adapted in accordance with the parameter set of the patient image to which each atlas image is to be matched, i.e. the visual appearance of the atlas image α is adapted so as to approach the visual appearance of the patient image 1 by using the parameter set associated with the patient image 1, and the representation information of the atlas image γ is determined on the basis of the parameter set associated with the patient image 2 in order to approach the visual appearance of the patient image 2. The matching transformation APT is then determined which can comprise sub-transformations APT1 and APT2 which are coupled with respect to the spatial information, in particular with respect to deformation. If, in particular, the patient images 1 and 2 exhibit the same spatial information or there is only a slight deviation between the patient image 1 and the patient image 2, then the patient images 1 and 2 can be assumed to be spatially identical. As a consequence, there is a constraint on the determination of APT. In the example given, the constraint would be that the deformation described by APT1 is the same as the deformation described by APT2.

Figure 5:
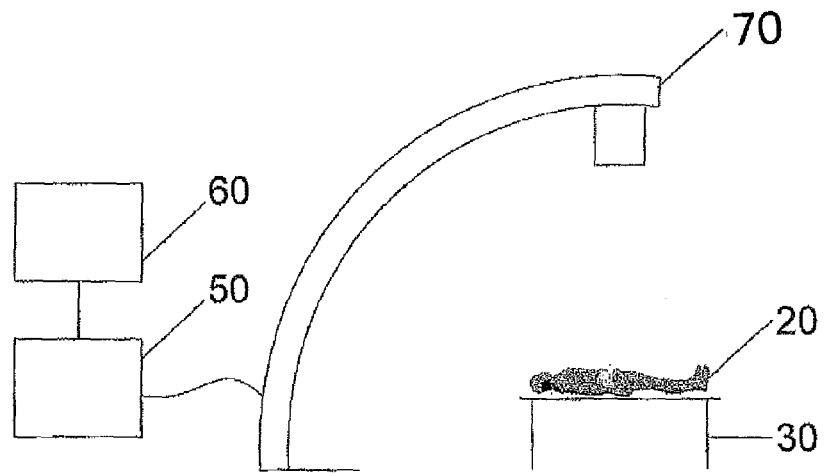
FIG. 5 shows a medical image processing system in accordance with the invention.

FIG. 5 shows a medical image processing system in which a patient 20 lies on a couch 30 and an analytical device 70 is provided in order to generate an analytical image of the patient 20. The analytical device 70 is connected to a computer 50 which comprises a monitor 60. The computer 50 is used to run a program which performs the data processing method as described in this document (i.e. "improvement method" and/or "matching method"), in order in particular to display atlas images and/or patient images and/or matched atlas images on the monitor 60.

Figure 6:
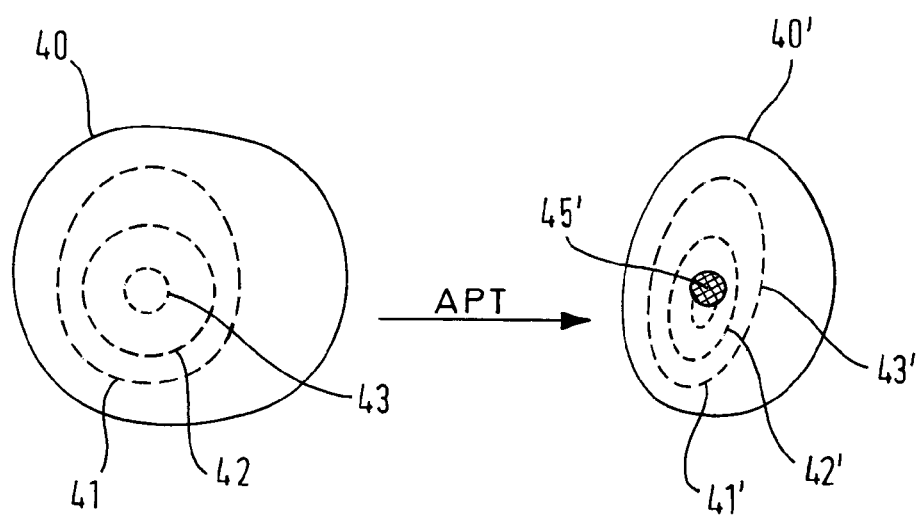

FIG. 6 illustrates how spatial meta information are matched. A white atlas element 40 is shown on the left in FIG. 4, which is combined with spatial meta information on the pathological changes. The spatial meta information is represented by contour lines 41, 42 and 43 which represent lines of constant probability for a pathological change along the line if the atlas element is associated with a particular patho parameter (for instance, a particular TNM classification). For instance, the probability of a tumour inside the contour line 41 is more than 10%, the probability of a tumour inside the contour line 42 is more than 50% and the probability of a tumour inside the contour line 43 is more than 90%. The determined matching transformation is then applied to the atlas element 40 and matches the atlas element 40 to the patient element 40' which has already been segmented, for instance using the corresponding method described in this document. The matching transformation is also applied to the spatial meta information. In the example given, the matching transformation is also applied to the contour lines, resulting in the matched contour lines 41', 42' and 43', i.e. the image on the right in FIG. 4 reflects a spatial statistical probability distribution of pathological changes. This image can be overlaid with the actual image of the patient, which then for example highlights an identified pathological change in the cross-hatched area 45'. Radiotherapy can for example be planned on the basis of the combined images. Radiotherapy can for example be planned not only on the basis of the cross-hatched area 45' but also on the basis of the contour lines 41', 42' and/or 43'. It is for example possible to plan for the application of the radiotherapy treatment to be expanded to the area within the contour line 42' in order to suppress possible pathological changes which cannot yet be identified by means of analytical images. Conversely, if the total patient element 40' is usually treated, the application of the radiotherapy treatment can be restricted to the area within the contour line 41'.

The present invention also pertains to the following additional embodiments, which also form part of the present description.

1. A data processing method for determining a matching transformation for matching a set of one or more images of an anatomical body structure of a patient, referred to as a patient image set, and a set of one or more images of a general anatomical structure, referred to as an atlas image set, wherein the general anatomical structure comprises a plurality of anatomical elements referred to as atlas elements, and each patient image is associated with one of a plurality of different parameter sets, wherein the parameter sets comprise one or more parameters which obtain when the patient images are generated, and the parameters influence representations of anatomical elements in the patient images, the method comprising the following steps performed by a computer:
  acquiring atlas data (S110, S120), comprising the steps of
    acquiring atlas spatial information (S110) which contains spatial information on the general anatomical structure, and
    acquiring element representation information (S120) which describes a plurality (in particular, a multitude) of representation data sets (Table 3) which contain information on representations of the plurality of atlas elements in the atlas images to be determined, wherein the element representation information describes a determination rule (S124) for determining respective representation data sets for respective atlas elements in accordance with different respective parameter sets;
  acquiring patient data (S130), comprising the sub-steps of
    acquiring the patient image set (S131), and
    acquiring one or more of the plurality of parameter sets (S132) which are respectively associated with the one or more images of the patient image set;
  determining (S140), on the basis of the atlas data and the patient data, the set of atlas images which respectively represent at least a part of the general anatomical structure by using (S141b) the spatial information on the general anatomical structure and particular representation data sets which are determined (S142) by applying the determination rule (S143) in accordance with the one or more associated parameter sets and particular atlas elements acquired (S141a) and referred to as corresponding elements, which are to be matched to corresponding anatomical elements represented in the patient image;
  determining (S150) the matching transformation (APT; APT1, APT2) which matches the atlas image set and the patient image set, by matching images associated with the same parameter set to each other.

2. The data processing method according to Embodiment 1, wherein determining the atlas image set involves:
  determining (S142) the representation data sets (Table 4) for the corresponding elements, wherein for each atlas image to be determined, one of the representation data sets is determined for each of the corresponding elements in accordance with the determination rule, wherein the determination rule comprises an assignment rule (S121, Table 1, S122, Table 2) for assigning a respective representation data set to a respective corresponding element in accordance with the parameter set associated with the patient image to which the atlas image which includes the corresponding element is to be matched; and
  determining the atlas image set (S143) comprising one or more images which are respectively associated with one of the parameter sets, by respectively using (S142) the determined representation data sets (Table 4) to determine the representations of the corresponding elements.

3. The data processing method according to any one of the preceding embodiments, wherein in order to determine the representation of one or more of the corresponding elements in the one or more atlas images, image values of patient elements are used in combination with determining the matching transformation.

4. The data processing method according to any one of the preceding embodiments, wherein the step (S150) of determining the matching transformation, which matches one of the atlas images and one of the patient images associated with one of the parameter sets to each other, is configured such that the matching transformation is determined on the basis of information on the matching transformation between another of the atlas images and another of the patient images associated with another of the associated parameter sets (FIG. 3).

5. The data processing method according to any one of the preceding embodiments, wherein the matching transformation is constituted to deform a part of the geometry of the general anatomical structure in order to match the atlas images to the patient images, and wherein determining the matching transformation involves taking into account information on the influence on matching quality of a deformation of at least one of the atlas images associated with at least one of the parameter sets in order to determine the deformation of at least another of the atlas images which is associated with at least another of the parameter sets and includes corresponding elements which are identical to the corresponding elements included in said at least one of the atlas images.

6. The data processing method according to the preceding embodiment, wherein determining the matching transformation involves taking into account the fact that the spatial information described by the atlas images is identical and also taking into account information on the spatial correlation between the spatial information described by the patient images in order to determine deformations described by the matching transformation which is applied in order to match the atlas images and patient images to each other.

7. The data processing method according to any one of the preceding embodiments, wherein the matching transformation (APT) comprises a set of coupled transformations referred to as matching sub-transformations (APT1, APT2), wherein the respective matching sub-transformations (APT1, APT2) respectively match the atlas images associated with one of the associated parameter sets and the patient image which is associated with the same respective associated parameter set to each other, and the matching sub-transformations are coupled in that they each influence the determination of the other.

8. The data processing method according to any one of the preceding embodiments, wherein the determination rule describes an assignment between the plurality of atlas elements and the plurality of representation data sets by describing a surjective assignment between the atlas elements and representation classes, wherein the respective representation classes respectively represent subsets of the plurality of representation data sets, and wherein for each of the respective representation classes, there is a unique set of characteristic bijective assignments between individual representation data sets of the subsets and individual parameter sets.

9. The data processing method according to any one of the preceding embodiments, wherein the representation data sets describe at least one of the following types of information on representation: image values for the anatomical elements; ranges of image values for the anatomical elements; the relationship between image values of different anatomical elements; the relationship between image values for one or more of the anatomical elements represented in images associated with different parameter sets; maximum image values for the anatomical elements; minimum image values for the anatomical elements; average image values for the anatomical elements; standard deviations of the average image values and structures of modulations of the image values for the anatomical elements; characteristics of transitions between representations of different anatomical elements.

10. The data processing method according to any one of the preceding embodiments, wherein the atlas data also comprise spatial flexibility information on a description of a flexibility of the position of atlas elements within the general anatomical structure, and wherein the matching transformation is determined on the basis of the spatial flexibility information.

11. The data processing method according to any one of the preceding embodiments, further comprising the step of acquiring correspondence part data which describe the corresponding elements, wherein the acquisition step involves acquiring coarse atlas spatial information on a description of the spatial information on the general anatomical structure in less detail than the atlas spatial information used to determine the atlas image set, wherein the acquisition step also involves applying a rigid matching transformation for matching the at least one patient image to a part of the general anatomical structure described by the coarse atlas spatial information, in order to determine the part of the general anatomical structure which allows a predetermined optimum of the matching result to be achieved, in particular a predetermined optimum of a measure of similarity, when determining the matching transformation, and wherein the corresponding elements are determined on the basis of the atlas elements included in the determined part.

12. The data processing method according to any one of the preceding embodiments, wherein the atlas spatial information comprises a description of a plurality of different states of the general anatomical structure which are respectively described by different sets of spatial information, wherein the plurality of different states correspond in particular to a time-dependent set of spatial information which in particular comprises a description of a time-dependent vital movement of at least part of the general anatomical structure, wherein acquiring the correspondence part data involves determining the state and in particular time, which allows a predetermined optimum of the matching result to be achieved, in particular a predetermined optimum of a measure of similarity, when determining the matching transformation.

13. The data processing method according to any one of the preceding embodiments, comprising the step of applying the matching transformation to the atlas image set in order to determine matched atlas images or applying the matching transformation to the patient image set in order to determine matched patient images.

14. A data processing method for determining a matching transformation for matching an image of an anatomical body structure of a patient, referred to as a patient image, and an image of a general anatomical structure, referred to as an atlas image, both the anatomical body structure of the patient and the general anatomical structure comprising pathological changes, wherein the patient image being associated with one of a plurality of different parameters referred to as patho parameters, wherein the patho parameters specify the pathological changes in accordance with a classification, the method comprising the following steps performed by a computer:

acquiring atlas data which contains information on a description of a plurality of images of the general anatomical structure for a plurality of patho parameters and in particular spatial meta information on the pathological changes, and acquiring patient data, comprising the sub-steps of
acquiring the patient image, and
acquiring the patho parameter associated with the patient image;

determining, on the basis of the atlas data and the patient data, the atlas image which represents at least a part of the general anatomical structure which comprises pathological changes in accordance with the patho parameter and which part corresponds to at least a part of the anatomical structure represented on the patient image; and determining the matching transformation which matches the atlas image and the patient image, and in particular which matches the spatial meta information to the patient image.

15. The data processing method of the preceding embodiment, wherein the method is for determining a matching transformation for matching a set of one or more images of the anatomical body structure of the patient associated with the same patho parameter, referred to as a patient image set, and a set of one or more images of the general anatomical structure, referred to as an atlas image set, wherein the general anatomical structure comprises a plurality of anatomical elements referred to as atlas elements, and each patient image is associated with one of a plurality of different parameter sets, wherein the parameter sets comprise one or more parameters which obtain when the patient images are generated, and the parameters influence representations of anatomical elements in the patient images, wherein the information on the description of an atlas image is a plurality of spatial information on a plurality of general anatomic structures respectively associated with one of the plurality of patho parameters, the step of acquiring atlas data comprises:

acquiring atlas spatial information which contains a plurality of spatial information on the general anatomical structure for a plurality of patho parameters, and acquiring element representation information which describes a plurality (in particular, a multitude) of representation data sets which contain information on representations of the plurality of atlas elements in the atlas images to be determined for a plurality of patho parameters, wherein the element representation information describes a determination rule for determining respective representation data sets for respective atlas elements in accordance with different respective parameter sets and in accordance with the patho parameter associated with the set of patient images;

the step of acquiring patient data comprising the sub-steps of acquiring one or more of the plurality of parameter sets which are respectively associated with the one or more images of the patient image set and which are respectively associated with the same patho parameter;

determining, on the basis of the atlas data and the patient data, the set of atlas images which respectively represent at least a part of the general anatomical structure associated with the patho parameter by using the spatial information on the general anatomical structure associated with the patho parameter and particular representation data sets associated with the patho parameter which are determined by applying the determination rule in accordance with the patho parameter and one or more associated parameter sets and particular atlas elements acquired and referred to as corresponding elements, which are to be matched to corresponding anatomical elements represented in the patient image;

determining the matching transformation which matches the atlas image set and the patient image set, by matching images associated with the same parameter set and the same patho parameter to each other;

the method in particular comprising the steps as described in any one of embodiments 2 to 13.

16. A program which, when running on a computer or when loaded onto a computer, causes the computer to perform the method steps of the method according to any one of the preceding embodiments and/or a program storage medium on which the program is stored and/or a computer on which the program is running or into the memory of which the program is loaded and/or a signal wave, in particular a digital signal wave, carrying information which represents the program.

17. A medical image processing system, comprising:
analytical devices for generating patient images of a patient; and
a computer according to the preceding embodiment which is constituted to determine the matching transformation and apply the matching transformation in order to match the generated patient images and determined atlas images.

The invention claimed is:

1. A data processing method for determining data which are referred to as atlas data and comprise information on a description of an image of a general anatomical structure, wherein this image is referred to as the atlas image, the method comprising the following steps performed by a computer:

acquiring patient data which comprise a description of a set of images of an anatomical structure of a set of associated patients, wherein the images are referred to as patient images and each patient image is associated with a parameter set which comprises one or more parameters given when the patient images are generated, wherein the parameters influence representations of anatomical elements as expressed by image values in the patient images, the patient data comprising the patient image set and the parameter sets associated with the patient image set;

acquiring model data which comprise information on a description of an image of a model of an anatomical structure of a patient which is referred to as the model image and is associated with the parameter set, the model data describing an anatomical atlas to be improved by the data processing method;

wherein the model of an anatomical structure is referred to as the model structure and comprises models of a plurality of anatomical elements which are referred to as model elements;

wherein the model data comprise:
model spatial information on a description of the spatial information on the model structure; and/or
model element representation information on a description of a plurality of representation data sets which contain information on representations of the plurality of model elements in the model images to be determined and are referred to as model representation data sets, wherein the model element representation information also describes a determination rule for determining respective model representation data sets for respective model elements in accordance with respective parameter sets;

wherein acquiring the model data involves determining, on the basis of the model data and the patient data, the set of model images which respectively represent at least a part of the model structure by using the spatial information on the model structure and particular model representation data sets which are determined by applying the determination rule in accordance with the one or more associated parameter sets and particular model elements referred to as corresponding model elements, which are to be matched to corresponding anatomical elements represented in the patient image and referred to as patient elements;

determining matching transformations which are referred to as PM transformations and which are constituted to respectively match the set of patient images of the set of patients to the set of determined model images by matching images associated with the same parameter set;

determining an inverse average transformation by applying an inverting and averaging operation to the determined PM transformations; and determining the atlas data by:
applying the determined inverse average transformation to the model data; or
respectively applying the determined PM transformations to the respective patient images in order to determine matched patient images, averaging the matched patient images in order to determine an average matched patient image, and determining the atlas data by applying the determined inverse average transformation to the average matched patient image.

2. The data processing method according to claim 1, wherein the inverting and averaging operation is applied by:
a) applying an inverting operation to the determined PM transformations in order to determine inverse PM transformations and then applying an averaging operation in order to average the inverse PM transformations and so determine the inverse average transformation; and/or
b) applying an averaging operation to the determined PM transformations in order to determine an average PM transformation and then applying an inverting operation in order to invert the average PM transformation and so determine the inverse average transformation.

3. The data processing method according to claim 1, wherein the patient data comprise a plurality of patient images associated with the same parameter set, which is referred to as the common parameter set, wherein acquiring the model data involves acquiring a model image associated with the common parameter set, and determining the atlas data involves applying the inverse average transformation to the model image in order to determine the atlas image associated with the common parameter set.

4. The data processing method according to claim 1, wherein determining the atlas data involves:
applying the determined inverse average transformation to the model spatial information in order to determine atlas spatial information on a description of spatial information for the general anatomical structure; and/or
applying the determined inverse average transformation to the model element representation information in order to determine atlas element representation information on a description of a plurality of atlas representation data sets which contain information on representations of atlas elements in atlas images, wherein the atlas elements are anatomical elements which the general anatomical structure comprises, and the representation data sets allow the representations of the atlas elements in atlas images to be determined.

5. The data processing method according to claim 4, wherein applying the inverse average transformation to the model spatial information involves or consists of applying the inverse average transformation to the part of the model spatial information on a description of the corresponding model elements, wherein applying the inverse average transformation to the corresponding model elements results in determined corresponding atlas elements.

6. The data processing method according to claim 4, wherein applying the determined inverse average transformation to the model element representation information involves or consists of applying the inverse average transformation to the particular model representation data sets, wherein applying the inverse average transformation to the particular model representation data sets results in the atlas representation data sets.

7. The data processing method according to claim 1, wherein if different parameter sets are associated with the patient images, then in order to apply the determined inverse average transformation to the model element representation information, at least the part of the inverse average transformation which relates to transforming representation information is determined separately for the different parameter sets, and wherein the respectively determined atlas representation information is respectively assigned to the respective parameter set.

8. The data processing method according to claim 1, wherein if different parameter sets are associated with the patient images, then in order to apply the determined inverse average transformation to the model spatial information, the averaging operation is applied to the PM transformation or inverse PM transformation separately for the different parameter sets in order to determine an average for the different parameter sets, and the averages are then weighted by weighting the local spatial part to which the transformations relate in accordance with the local amount of underlying image information available in the corresponding local spatial part of the patient images to be matched and/or in accordance with the combination of the respective parameter set and a type—in particular, a representation class—of a local model segment on which matching is performed.

9. The data processing method according to claim 1, wherein if different parameter sets are available and patient images of the same patient which represent the same patient elements but are associated with different parameters are available, then the PM transformations for the patient images referred to as coupled patient images (correspondingly referred to as coupled PM transformations), which match the different coupled patient images to the different model images, are constituted to take into account the fact that the spatial information described by the model images is identical and to also take into account information on the spatial correlation between the spatial information described by the different coupled patient images in order to determine deformations described by the coupled PM transformations.

10. The data processing method according to claim 1, wherein the determination rule describes an assignment between the plurality of model elements and the plurality of model representation data sets by describing a surjective assignment between the model elements and representation classes, wherein the respective representation classes respectively represent subsets of the plurality of model representation data sets, and wherein for each of the respective representation classes, there is a unique set of characteristic bijective assignments between individual model representation data sets of the subsets and individual parameter sets.

11. The data processing method according to claim 1, wherein the model representation data sets describe at least one of the following types of information on representation:
image values for the anatomical elements;
ranges of image values for the anatomical elements;
the relationship between image values of different anatomical elements;
the relationship between image values for one or more of the anatomical elements represented in images associated with different parameter sets;
maximum image values for the anatomical elements;
minimum image values for the anatomical elements; average image values for the anatomical elements;
standard deviations of the average image values and structures of modulations of the image values for the anatomical elements; and
characteristics of transitions between representations of different anatomical elements.

12. The data processing method according to claim 1, further comprising the step of acquiring model correspondence part data which describe the corresponding model elements, wherein acquiring the model correspondence part data involves acquiring coarse model spatial information on a description of the spatial information on the model structure in less detail than the model spatial information used for determining the model image set, and also involves applying a rigid matching transformation in order to match the at least one patient image to a part of the model structure described by the coarse model spatial information, in order to determine the part of the model structure which allows a predetermined optimum of the matching result to be achieved, in particular a predetermined optimum of a measure of similarity, when determining the PM transformations, and wherein the corresponding model elements are determined on the basis of the model elements included in the determined part.

13. The data processing method according to claim 1, wherein the model image is based on image analysis data which describe a set of analytical images representing the anatomical body structure of a set of patients and/or is based on a generic model of the anatomical body structure.

14. The data processing method according to claim 1, wherein the patient data comprise meta data which are referred to as patient patho meta data and describe parameters referred to as patho parameters, wherein the patho parameters specify a pathological change in the anatomical structure of the set of patients, and wherein the patho parameters which are assigned to the patient images on the basis of which the PM transformations are determined are preferably identical and the model image is preferably associated with the same patho parameter or is a neutral model image.

15. A program embodied on a non-transitory computer readable medium which, when running on a computer or when loaded onto a computer, causes the computer to determine data which are referred to as atlas data and comprise information on a description of an image of a general anatomical structure wherein this image is referred to as the atlas image, wherein the atlas data are determined by steps comprising:
acquiring patient data which comprise a description of a set of images of an anatomical structure of a set of associated patients, wherein the images are referred to as patient images and each patient image is associated with a parameter set which comprises one or more parameters given when the patient images are generated, wherein the parameters influence representations of anatomical elements as expressed by image values in the patient images, the patient data comprising the patient image set and the parameter sets associated with the patient image set;

acquiring model data which comprise information on a description of an image of a model of an anatomical structure of a patient which is referred to as the model image and is associated with the parameter set, the model data describing an anatomical atlas to be improved by the data processing method;

wherein the model of an anatomical structure is referred to as the model structure and comprises models of a plurality of anatomical elements which are referred to as model elements;

wherein the model data comprise:
model spatial information on a description of the spatial information on the model structure; and/or
model element representation information on a description of a plurality of representation data sets which contain information on representations of the plurality of model elements in the model images to be determined and are referred to as model representation data sets, wherein the model element representation information also describes a determination rule for determining respective model representation data sets for respective model elements in accordance with respective parameter sets;

wherein acquiring the model data involves determining, on the basis of the model data and the patient data, the set of model images which respectively represent at least a part of the model structure by using the spatial information on the model structure and particular model representation data sets which are determined by applying the determination rule in accordance with the one or more associated parameter sets and particular model elements referred to as corresponding model elements, which are to be matched to corresponding anatomical elements represented in the patient image and referred to as patient elements;

determining matching transformations which are referred to as PM transformations and which are constituted to respectively match the set of patient images of the set of patients to the set of determined model images by matching images associated with the same parameter set;

determining an inverse average transformation by applying an inverting and averaging operation to the determined PM transformations; and determining the atlas data by:
applying the determined inverse average transformation to the model data; or
respectively applying the determined PM transformations to the respective patient images in order to determine matched patient images, averaging the matched patient images in order to determine an average matched patient image, and determining the atlas data by applying the determined inverse average transformation to the average matched patient image.

16. A non-transitory program storage medium on which a program is stored which, when running on a computer or when loaded onto a computer, causes the computer to determine data which are referred to as atlas data and comprise information on a description of an image of a general anatomical structure, wherein this image is referred to as the atlas image, wherein the atlas data are determined by steps comprising:

acquiring patient data which comprise a description of a set of images of an anatomical structure of a set of associated patients, wherein the images are referred to as patient images and each patient image is associated with a parameter set which comprises one or more parameters given when the patient images are generated, wherein the parameters influence representations of anatomical elements as expressed by image values in the patient images, the patient data comprising the patient image set and the parameter sets associated with the patient image set;

acquiring model data which comprise information on a description of an image of a model of an anatomical structure of a patient which is referred to as the model image and is associated with the parameter set, the model data describing an anatomical atlas to be improved by the data processing method;

wherein the model of an anatomical structure is referred to as the model structure and comprises models of a plurality of anatomical elements which are referred to as model elements;

wherein the model data comprise:
model spatial information on a description of the spatial information on the model structure; and/or
model element representation information on a description of a plurality of representation data sets which contain information on representations of the plurality of model elements in the model images to be determined and are referred to as model representation data sets, wherein the model element representation information also describes a determination rule for determining respective model representation data sets for respective model elements in accordance with respective parameter sets;

wherein acquiring the model data involves determining, on the basis of the model data and the patient data, the set of model images which respectively represent at least a part of the model structure by using the spatial information on the model structure and particular model representation data sets which are determined by applying the determination rule in accordance with the one or more associated parameter sets and particular model elements referred to as corresponding model elements, which are to be matched to corresponding anatomical elements represented in the patient image and referred to as patient elements;

determining matching transformations which are referred to as PM transformations and which are constituted to respectively match the set of patient images of the set of patients to the set of determined model images by matching images associated with the same parameter set;

determining an inverse average transformation by applying an inverting and averaging operation to the determined PM transformations; and determining the atlas data by:
applying the determined inverse average transformation to the model data; or
respectively applying the determined PM transformations to the respective patient images in order to determine matched patient images, averaging the matched patient images in order to determine an average matched patient image, and determining the atlas data by applying the determined inverse average transformation to the average matched patient image.

17. A computer comprising the non-transitory program storage medium of claim 16.

18. A medical image processing system, comprising:
one or more analytical devices for generating patient images of an associated patient; and
a computer according to claim 17 which is constituted to determine the atlas data based on the generated patient images.

\* \* \* \* \*